(12) United States Patent
Xavier et al.

(10) Patent No.: US 12,046,361 B2
(45) Date of Patent: *Jul. 23, 2024

(54) TAGGING PUMP MESSAGES WITH IDENTIFIERS THAT FACILITATE RESTRUCTURING

(71) Applicant: ICU Medical, Inc., San Clemente, CA (US)

(72) Inventors: Ben Xavier, San Diego, CA (US); Dennis Krabbe, San Diego, CA (US); Larry Enger, Oceanside, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,627

(22) Filed: Apr. 28, 2023

(65) Prior Publication Data

US 2024/0071606 A1 Feb. 29, 2024

Related U.S. Application Data

(63) Continuation of application No. 17/447,560, filed on Sep. 13, 2021, now Pat. No. 11,670,416, which is a
(Continued)

(51) Int. Cl.
*G16H 40/20* (2018.01)
*A61M 5/142* (2006.01)
(Continued)

(52) U.S. Cl.
CPC ............ *G16H 40/20* (2018.01); *A61M 5/142* (2013.01); *A61M 5/172* (2013.01);
(Continued)

(58) Field of Classification Search
CPC ........ G16H 40/20; G16H 20/17; G16H 40/40; G16H 40/60; G16H 40/63; G16H 40/67;
(Continued)

(56) References Cited

U.S. PATENT DOCUMENTS

| 4,024,864 A | 5/1977 | Davies et al. |
| 4,055,175 A | 10/1977 | Clemens et al. |

(Continued)

FOREIGN PATENT DOCUMENTS

| AU | 2004226440 | 10/2004 |
| AU | 2004305087 | 7/2005 |

(Continued)

OTHER PUBLICATIONS

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.
(Continued)

*Primary Examiner* — Abdullahi E Salad
(74) *Attorney, Agent, or Firm* — Knobbe, Martens, Olson & Bear, LLP

(57) ABSTRACT

Various techniques for facilitating communication with and across a clinical environment and a cloud environment are described. For example, a method for tagging messages with facility identifiers in a manner that does not require changing the identifiers when logically re-arranging the facilities. A connectivity adapter in the clinical environment can receive a message from an infusion pump and tag the message with only permanent IDs such that when the facility in which the connectivity resides is categorized under a different system or region, the identifiers in the message need not be updated.

20 Claims, 13 Drawing Sheets

Related U.S. Application Data continuation of application No. 16/914,147, filed on Jun. 26, 2020, now Pat. No. 11,152,110, which is a continuation of application No. 16/512,308, filed on Jul. 15, 2019, now Pat. No. 10,741,280, which is a continuation of application No. PCT/US2019/041706, filed on Jul. 12, 2019.

(60) Provisional application No. 62/699,499, filed on Jul. 17, 2018.

(51) Int. Cl.
| | |
|---|---|
| *A61M 5/172* | (2006.01) |
| *G06F 12/0802* | (2016.01) |
| *G06F 16/2455* | (2019.01) |
| *G16H 20/17* | (2018.01) |
| *G16H 40/40* | (2018.01) |
| *G16H 40/60* | (2018.01) |
| *G16H 40/63* | (2018.01) |
| *G16H 40/67* | (2018.01) |
| *G16H 80/00* | (2018.01) |
| *H04L 9/40* | (2022.01) |
| *H04L 43/0811* | (2022.01) |
| *H04L 43/16* | (2022.01) |
| *H04L 67/00* | (2022.01) |
| *H04L 67/125* | (2022.01) |
| *H04L 67/565* | (2022.01) |
| *H04L 67/5682* | (2022.01) |
| *H04L 69/08* | (2022.01) |
| *H04L 69/18* | (2022.01) |
| *H04L 67/10* | (2022.01) |

(52) U.S. Cl.
CPC .... *G06F 12/0802* (2013.01); *G06F 16/24552* (2019.01); *G16H 20/17* (2018.01); *G16H 40/40* (2018.01); *G16H 40/60* (2018.01); *G16H 40/63* (2018.01); *G16H 40/67* (2018.01); *G16H 80/00* (2018.01); *H04L 43/0811* (2013.01); *H04L 43/16* (2013.01); *H04L 63/08* (2013.01); *H04L 67/125* (2013.01); *H04L 67/34* (2013.01); *H04L 67/565* (2022.05); *H04L 67/5682* (2022.05); *H04L 69/08* (2013.01); *H04L 69/18* (2013.01); *A61M 2005/14208* (2013.01); *A61M 2205/18* (2013.01); *A61M 2205/3553* (2013.01); *A61M 2205/3561* (2013.01); *A61M 2205/3584* (2013.01); *A61M 2205/3592* (2013.01); *A61M 2205/52* (2013.01); *H04L 67/10* (2013.01)

(58) Field of Classification Search
CPC ....... G16H 80/00; A61M 5/142; A61M 5/172; A61M 2005/14208; A61M 2205/18; A61M 2205/3553; A61M 2205/3561; A61M 2205/3584; A61M 2205/3592; A61M 2205/52; G06F 12/0802; G06F 16/24552; H04L 43/0811; H04L 43/16; H04L 63/08; H04L 67/125; H04L 67/34; H04L 67/565; H04L 67/5682; H04L 69/08; H04L 69/18; H04L 67/10
See application file for complete search history.

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,730,849 A | 3/1988 | Siegel |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |

(56) References Cited

U.S. PATENT DOCUMENTS

| | | |
|---|---|---|
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,708,714 A | 1/1998 | Lopez et al. |
| 5,713,350 A | 2/1998 | Yokota et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,024,699 A | 2/2000 | Surwit et al. |
| 6,032,155 A | 2/2000 | de la Huerga |
| 6,032,676 A | 3/2000 | Moore |
| 6,039,251 A | 3/2000 | Holowko et al. |
| 6,070,761 A | 6/2000 | Bloom et al. |
| 6,073,106 A | 6/2000 | Rozen et al. |
| 6,104,295 A | 8/2000 | Gaisser et al. |
| 6,112,182 A | 8/2000 | Akers et al. |
| 6,112,323 A | 8/2000 | Meizlik et al. |
| RE36,871 E | 9/2000 | Epstein et al. |
| 6,115,365 A | 9/2000 | Newberg |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |

(56) References Cited

U.S. PATENT DOCUMENTS

| | | |
|---|---|---|
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de La Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |

(56) References Cited

U.S. PATENT DOCUMENTS

| | | |
|---|---|---|
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 * | 1/2007 | Chung .................. H01Q 7/00 340/5.1 |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,436,454 B2 | 10/2008 | Yamaguchi et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,469,213 B1 | 12/2008 | Rao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,788,369 B2 | 8/2010 | McAllen et al. |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,864,771 B2 | 1/2011 | Tavares et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 * | 1/2012 | Mehta ................ H04L 61/5038 370/395.3 |
| 8,126,730 B2 | 2/2012 | Dicks et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |

(56) References Cited

U.S. PATENT DOCUMENTS

| | | | |
|---|---|---|---|
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,472,630 B2 | 6/2013 | Konrad et al. |
| 8,480,648 B2 | 7/2013 | Burnett et al. |
| 8,486,019 B2 | 7/2013 | White et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,567,681 B2 | 10/2013 | Borges et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,667,293 B2 | 3/2014 | Birtwhistle et al. |
| 8,687,811 B2 | 4/2014 | Nierzwick et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,886,316 B1 | 11/2014 | Juels |
| 8,922,330 B2 | 12/2014 | Moberg et al. |
| 8,936,565 B2 | 1/2015 | Chawla |
| 8,945,043 B2 | 2/2015 | Lee et al. |
| 8,952,794 B2 | 2/2015 | Blomquist et al. |
| 8,959,617 B2 | 2/2015 | Newlin et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 | 3/2016 | Wallrabenstein |
| 9,302,035 B2 | 4/2016 | Marseille et al. |
| 9,313,154 B1 | 4/2016 | Son |
| 9,381,296 B2 | 7/2016 | Arrizza et al. |
| 9,393,362 B2 | 7/2016 | Cozmi et al. |
| 9,430,655 B1 | 8/2016 | Stockton et al. |
| 9,483,615 B2 * | 11/2016 | Roberts .............. G16H 40/20 |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,717,845 B2 | 8/2017 | Istoc |
| 9,724,470 B2 | 8/2017 | Day et al. |
| 9,764,082 B2 | 9/2017 | Day et al. |
| 9,886,550 B2 | 2/2018 | Lee et al. |
| 9,943,269 B2 | 4/2018 | Muhsin et al. |
| 9,967,739 B2 | 5/2018 | Proennecke et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,173,008 B2 * | 1/2019 | Simpson ................ G16H 10/60 |
| 10,188,849 B2 | 1/2019 | Fangrow |
| 10,233,179 B2 | 3/2019 | Ng et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,341,866 B1 | 7/2019 | Spencer et al. |
| 10,430,761 B2 | 10/2019 | Hume et al. |
| 10,434,246 B2 | 10/2019 | Silkaitis et al. |
| 10,453,157 B2 | 10/2019 | Kamen et al. |
| 10,463,788 B2 | 11/2019 | Day |
| 10,516,536 B2 | 12/2019 | Rommel |
| 10,617,815 B2 | 4/2020 | Day et al. |
| 10,646,651 B2 | 5/2020 | Day et al. |
| 10,681,207 B1 | 6/2020 | Johnson et al. |
| 10,692,595 B2 | 6/2020 | Xavier et al. |
| 10,740,436 B2 | 8/2020 | Moskal et al. |
| 10,741,280 B2 | 8/2020 | Xavier et al. |
| 10,757,219 B2 | 8/2020 | Moskal |
| 10,765,799 B2 | 9/2020 | Belkin et al. |
| 10,799,632 B2 | 10/2020 | Kohlbrecher |
| 10,812,380 B2 | 10/2020 | Jha et al. |
| 10,861,592 B2 | 12/2020 | Xavier et al. |
| 10,898,641 B2 | 1/2021 | Day et al. |
| 10,950,339 B2 | 3/2021 | Xavier et al. |
| 10,964,428 B2 | 3/2021 | Xavier et al. |
| 11,013,861 B2 | 5/2021 | Wehba et al. |
| 11,037,668 B2 | 6/2021 | Ruchti et al. |
| 11,052,193 B2 | 7/2021 | Day et al. |
| 11,139,058 B2 | 10/2021 | Xavier et al. |
| 11,151,290 B2 | 10/2021 | Karakoyunlu et al. |
| 11,152,108 B2 | 10/2021 | Xavier et al. |
| 11,152,109 B2 | 10/2021 | Xavier et al. |
| 11,152,110 B2 | 10/2021 | Xavier et al. |
| 11,194,810 B2 | 12/2021 | Butler et al. |
| 11,235,100 B2 | 2/2022 | Howard et al. |
| 11,289,183 B2 | 3/2022 | Kohlbrecher |
| 11,309,070 B2 | 4/2022 | Xavier et al. |
| 11,328,804 B2 | 5/2022 | Xavier et al. |
| 11,328,805 B2 | 5/2022 | Xavier et al. |
| 11,373,753 B2 | 6/2022 | Xavier et al. |
| 11,437,132 B2 | 9/2022 | Xavier et al. |
| 11,470,000 B2 | 10/2022 | Jha et al. |
| 11,483,402 B2 | 10/2022 | Xavier et al. |
| 11,483,403 B2 | 10/2022 | Xavier et al. |
| 11,501,877 B2 | 11/2022 | Kohlbrecher et al. |
| 11,571,508 B2 | 2/2023 | Jacobson et al. |
| 11,574,721 B2 | 2/2023 | Kohlbrecher |
| 11,574,737 B2 | 2/2023 | Dharwad et al. |
| 11,587,669 B2 | 2/2023 | Xavier et al. |
| 11,590,057 B2 | 2/2023 | Tagliamento et al. |
| 11,594,326 B2 | 2/2023 | Xavier et al. |
| 11,605,468 B2 | 3/2023 | Jacobson et al. |
| 11,626,205 B2 | 4/2023 | Arrizza et al. |
| 11,628,246 B2 | 4/2023 | Day et al. |
| 11,628,254 B2 | 4/2023 | Day et al. |
| 11,654,237 B2 | 5/2023 | Wehba et al. |
| 11,670,416 B2 | 6/2023 | Xavier et al. |
| 11,763,927 B2 | 9/2023 | Ruchti et al. |
| 11,783,935 B2 | 10/2023 | Xavier et al. |
| 2001/0013854 A1 | 8/2001 | Ogoro |
| 2001/0016056 A1 | 8/2001 | Westphal et al. |

(56) References Cited

U.S. PATENT DOCUMENTS

| | | |
|---|---|---|
| 2001/0029178 A1 | 10/2001 | Criss et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013551 A1 | 1/2002 | Zaitsu et al. |
| 2002/0013723 A1 | 1/2002 | Mise |
| 2002/0015018 A1 | 2/2002 | Shimazu et al. |
| 2002/0016568 A1 | 2/2002 | Lebel et al. |
| 2002/0019584 A1 | 2/2002 | Schulze et al. |
| 2002/0021700 A1 | 2/2002 | Hata et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0038206 A1 | 3/2002 | Dori |
| 2002/0038392 A1 | 3/2002 | de la Huerga |
| 2002/0040208 A1 | 4/2002 | Flaherty et al. |
| 2002/0040282 A1 | 4/2002 | Bailey et al. |
| 2002/0044043 A1 | 4/2002 | Chaco et al. |
| 2002/0044059 A1 | 4/2002 | Reeder et al. |
| 2002/0077852 A1 | 6/2002 | Ford et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0154600 A1 | 10/2002 | Ido et al. |
| 2002/0169636 A1 | 11/2002 | Eggers et al. |
| 2002/0173702 A1 | 11/2002 | Lebel et al. |
| 2002/0173875 A1 | 11/2002 | Wallace et al. |
| 2002/0193679 A1 | 12/2002 | Malave et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0036744 A1 | 2/2003 | Struys et al. |
| 2003/0047126 A1 | 3/2003 | Tomaschko |
| 2003/0047600 A1 | 3/2003 | Nakanishi et al. |
| 2003/0050621 A1 | 3/2003 | Lebel et al. |
| 2003/0052787 A1 | 3/2003 | Zerhusen et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0114836 A1 | 6/2003 | Estes et al. |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1* | 1/2004 | Carrender ........ G06K 19/07749 340/8.1 |
| 2004/0010786 A1 | 1/2004 | Cool et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |

(56) References Cited

U.S. PATENT DOCUMENTS

| | | |
|---|---|---|
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0137653 A1 | 6/2005 | Friedman et al. |
| 2005/0138428 A1 | 6/2005 | McAllen et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0026205 A1 | 2/2006 | Butterfield et al. |
| 2006/0042139 A1 | 3/2006 | Mendes |
| 2006/0047270 A1 | 3/2006 | Shelton |
| 2006/0047538 A1 | 3/2006 | Condurso et al. |
| 2006/0053036 A1 | 3/2006 | Coffman et al. |
| 2006/0064020 A1 | 3/2006 | Burnes et al. |
| 2006/0074463 A1 | 4/2006 | Seeberger et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229551 A1 | 10/2006 | Martinez et al. |
| 2006/0229918 A1 | 10/2006 | Fotsch et al. |
| 2006/0236373 A1 | 10/2006 | Graves et al. |
| 2006/0247606 A1 | 11/2006 | Batch |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |

(56) References Cited

U.S. PATENT DOCUMENTS

| | | |
|---|---|---|
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0077198 A1 | 3/2010 | Buck |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1* | 5/2010 | Portnoy ............ G06Q 10/1093 705/7.18 |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0204574 A1 | 8/2010 | Duchon et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0292645 A1 | 11/2010 | Hungerford et al. |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016295 A1 | 1/2012 | Tsoukalis |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0053533 A1 | 3/2012 | Butterfield et al. |
| 2012/0066501 A1 | 3/2012 | Xiong |
| 2012/0070045 A1 | 3/2012 | Vesper et al. |
| 2012/0095437 A1 | 4/2012 | Hemmerling |
| 2012/0112903 A1 | 5/2012 | Kaib et al. |

(56) References Cited

U.S. PATENT DOCUMENTS

| | | |
|---|---|---|
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0172802 A1 | 7/2012 | Blomquist et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0035633 A1 | 2/2013 | Chawla |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0138452 A1 | 5/2013 | Cork et al. |
| 2013/0144206 A1 | 6/2013 | Lee et al. |
| 2013/0150824 A1 | 6/2013 | Estes et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0058350 A1 | 2/2014 | Stewart et al. |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1 | 6/2014 | Kamen et al. |
| 2014/0194817 A1 | 7/2014 | Lee et al. |
| 2014/0197950 A1 | 7/2014 | Shupp et al. |
| 2014/0215490 A1 | 7/2014 | Mathur et al. |
| 2014/0221959 A1 | 8/2014 | Gray et al. |
| 2014/0254598 A1 | 9/2014 | Jha et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0288947 A1 | 9/2014 | Simpson et al. |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0366878 A1 | 12/2014 | Baron |
| 2014/0371543 A1 | 12/2014 | Steinhauer et al. |
| 2015/0001285 A1 | 1/2015 | Halbert et al. |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058960 A1 | 2/2015 | Schmoyer et al. |
| 2015/0066531 A1 | 3/2015 | Jacobson et al. |
| 2015/0081894 A1 | 3/2015 | Blomquist |
| 2015/0097701 A1 | 4/2015 | Al-Ali et al. |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0230760 A1 | 8/2015 | Schneider |
| 2015/0281128 A1 | 10/2015 | Sindhu |
| 2015/0328396 A1 | 11/2015 | Adams et al. |
| 2015/0352301 A1 | 12/2015 | Stedman et al. |
| 2015/0371004 A1 | 12/2015 | Jones |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0051749 A1 | 2/2016 | Istoc |
| 2016/0063471 A1 | 3/2016 | Kobres et al. |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2017/0034277 A1 | 2/2017 | Jackson et al. |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0146381 A1 | 5/2017 | Eckel et al. |
| 2017/0147761 A1 | 5/2017 | Moskal et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0258401 A1 | 9/2017 | Volpe |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0325091 A1 | 11/2017 | Freeman et al. |
| 2017/0351841 A1 | 12/2017 | Moskal |
| 2018/0063724 A1 | 3/2018 | Zhang et al. |
| 2018/0121613 A1 | 5/2018 | Connely, IV et al. |
| 2018/0122502 A1 | 5/2018 | Jones et al. |
| 2018/0126067 A1 | 5/2018 | Ledford et al. |
| 2018/0181712 A1* | 6/2018 | Ensey ............... G16H 50/20 |
| 2018/0247712 A1 | 8/2018 | Muhsin et al. |
| 2018/0272117 A1 | 9/2018 | Fangrow |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0147998 A1 | 5/2019 | Ruchti et al. |
| 2019/0166501 A1 | 5/2019 | Debates et al. |
| 2019/0172590 A1 | 6/2019 | Vesto et al. |
| 2019/0228863 A1 | 7/2019 | Dharwad et al. |
| 2019/0229982 A1 | 7/2019 | Ikuta et al. |
| 2019/0240405 A1 | 8/2019 | Wehba et al. |
| 2019/0243829 A1 | 8/2019 | Butler et al. |
| 2019/0244689 A1 | 8/2019 | Atkin |
| 2019/0245942 A1 | 8/2019 | Moskal |
| 2019/0269852 A1 | 9/2019 | Kohlbrecher |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |

(56) References Cited

U.S. PATENT DOCUMENTS

| | | | |
|---|---|---|---|
| 2020/0027541 A1 | 1/2020 | Xavier et al. |
| 2020/0027542 A1 | 1/2020 | Xavier et al. |
| 2020/0027543 A1 | 1/2020 | Xavier et al. |
| 2020/0027548 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |
| 2020/0028914 A1 | 1/2020 | Xavier et al. |
| 2020/0035346 A1 | 1/2020 | Xavier et al. |
| 2020/0035355 A1 | 1/2020 | Xavier et al. |
| 2020/0054825 A1 | 2/2020 | Kamen et al. |
| 2020/0061291 A1 | 2/2020 | Day et al. |
| 2020/0145332 A1 | 5/2020 | Jha et al. |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0306443 A1 | 10/2020 | Day |
| 2020/0330685 A1 | 10/2020 | Day |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0043296 A1 | 2/2021 | Xavier et al. |
| 2021/0045640 A1 | 2/2021 | Poltorak |
| 2021/0085855 A1 | 3/2021 | Belkin et al. |
| 2021/0098106 A1 | 4/2021 | Kohlbrecher et al. |
| 2021/0098107 A1 | 4/2021 | Xavier et al. |
| 2021/0105206 A1 | 4/2021 | Jha et al. |
| 2021/0252210 A1 | 8/2021 | Day et al. |
| 2021/0358603 A1 | 11/2021 | Xavier et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0023535 A1 | 1/2022 | Day |
| 2022/0037011 A1 | 2/2022 | Fryman |
| 2022/0037012 A1 | 2/2022 | Fryman |
| 2022/0051777 A1 | 2/2022 | Xavier et al. |
| 2022/0062541 A1 | 3/2022 | Kamen et al. |
| 2022/0129452 A1 | 4/2022 | Butler et al. |
| 2022/0139536 A1 | 5/2022 | Xavier et al. |
| 2022/0139537 A1 | 5/2022 | Xavier et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0270736 A1 | 8/2022 | Kohlbrecher |
| 2022/0328175 A1 | 10/2022 | Arrizza et al. |
| 2022/0331513 A1 | 10/2022 | Howard et al. |
| 2022/0344023 A1 | 10/2022 | Xavier et al. |
| 2022/0375565 A1 | 11/2022 | Xavier et al. |
| 2022/0384059 A1 | 12/2022 | Xavier et al. |
| 2023/0009405 A1 | 1/2023 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0166026 A1 | 6/2023 | Jacobson et al. |
| 2023/0188465 A1 | 6/2023 | Jha et al. |
| 2023/0253108 A1 | 8/2023 | Dharwad et al. |
| 2023/0285660 A1 | 9/2023 | Day et al. |
| 2023/0298768 A1 | 9/2023 | Jacobson et al. |
| 2023/0320935 A1 | 10/2023 | Tagliamento |
| 2023/0321350 A1 | 10/2023 | Day |
| 2023/0321351 A1 | 10/2023 | Wehba et al. |
| 2023/0326570 A1 | 10/2023 | Kohlbrecher |
| 2023/0410989 A1 | 12/2023 | Xavier et al. |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | I631966 | 8/2018 |
| WO | WO 84/001719 | 5/1984 |
| WO | WO 91/016416 | 10/1991 |
| WO | WO 92/010985 | 7/1992 |
| WO | WO 92/013322 | 8/1992 |

(56) References Cited

FOREIGN PATENT DOCUMENTS

| | | |
|---|---|---|
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/179389 | 11/2016 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/159134 | 8/2023 |

OTHER PUBLICATIONS

Murphy, Robert, "The Design of Safety-Critical Medical Infusion Devices", May 30, 2007, Doctor of Philosophy submission, pp. 317.
Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.
Ahn et al., "Towards Scalable Authentication in Health Services", Eleventh IEEE International Workshops on Enabling Technologies: Infrastructure for Collaborative Enterprises, Jun. 2002, pp. 83-88.
Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.
Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.
Beard et al., "Total Quality Pain Management: History, Background, Resources", Abbott Laboratories, TQPM Survey History, available Feb. 2015 or earlier, pp. 1-3.
Bektas et al., "Bluetooth Communication Employing Antenna Diversity", Proceedings of Eight IEEE International Symposium on Computers and Communication, Jul. 2003, pp. 6.
Bellare et al., "Security Proofs for Identity-Based Identification and Signature Schemes", Lecture Notes in Computer Science, Jan. 2009, vol. 22, No. 1, pp. 18.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.
Brownlee, Seth, "Product Spotlight: The Plum A+ with Hospira MedNet Infusion System", PP&P Magazine, Dec. 2005, vol. 2, No. 7, pp. 2.
Cannon, Md et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-_Service_Manual.pdf>.
"CareAware® Infusion Management", Cerner Store, as printed May 12, 2011, pp. 3, <https://store.cerner.com/items/7>.

(56) References Cited

OTHER PUBLICATIONS

Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.

"Context-Free Grammar", Wikipedia.org, as last modified Mar. 5, 2010 in 11 pages, <https://en.wikipedia.org/w/index.php/?title=Context-free_grammar&oldid=347915989>.

Crawford, Anne J., MSN, RNC, "Building a Successful Quality Pain Service: Using Patient Satisfaction Data and the Clinical Practice Guideline", USA, 1995, pp. 1-6.

Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Davies, T., "Cordless Data Acquisition in a Hospital Environment", IEE Colloquium on Cordless Computing—Systems and User Experience, 1993, pp. 4.

Dayhoff et al., "Medical Data Capture and Display: The Importance of Clinicians' Workstation Design", AMIA, Inc., 1994, pp. 541-545.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

Doesburg et al., "Improved Usability of a Multi-Infusion Setup Using a Centralized Control Interface: A Task-Based Usability Test", Aug. 11, 2017, PLoS ONE, vol. 12, No. 8, pp. 10.

"Download", Free On-Line Dictionary of Computing, as archived Jun. 16, 2010 in 1 page, http://web.archive.org/web/20100616010314/https://foldoc.org/download.

EAST PhD et al., "Digital Electronic Communication Between ICU Ventilators and Computers and Printers", Respiratory Care, Sep. 1992, vol. 37, No. 9, pp. 1113-1122.

Edworthy, Judy, "Medical Audible Alarms: A Review", Journal of the American Medical Informatics Association, vol. 20, No. 3, 2013, pp. 584-589.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Felleiter et al., "Data Processing in Prehospital Emergency Medicine", International journal of Clinical Monitoring and Computing, Feb. 1995, vol. 12, No. 1, pp. 37-41.

"File Verification", Wikipedia.org, as last modified Oct. 11, 2011 in 2 pages, <https://en.wikipedia.org/w/index.php?title=File_verification&oldid=455048290>.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

Gardner, Ph.D et al., "Real Time Data Acquisition: Recommendations for the Medical Information Bus (MIB)", 1992, pp. 813-817.

"General-Purpose Infusion Pumps", Health Devices, EXRI Institute, Oct. 1, 2002, vol. 31, No. 10, pp. 353-387.

Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.

Glaeser, "A Hierarchical Minicomputer System for Continuous Post-Surgical Monitoring", Computers and Biomedical Research, Aug. 31, 1975, pp. 336-361.

Goldberg et al., "Clinical Results of an Updated Insulin Infusion Protocol in Critically Ill Patients", Diabetes Spectrum, 2005, vol. 18, No. 3, pp. 188-191.

Gomez et al., "CLAM: Connection-Less, Lightweight, and Multiway Communication Support for Distributed Computing", Computer Science, 1997, vol. 1199, pp. 227-240.

"GPS Tracker for Medical Equipment", <http://www.trackingsystem.com/forbusinesses/corporate-trackingsystem/1098-gps-tracker-formedicalequipment.html>, Mar. 15, 2015, pp. 2.

Graseby, "Model 3000/500 and Micro 3100/505: Volumetric Infusion Pump", Technical Service Manual, Graseby Medical Ltd., Apr. 2002, Issue A, pp. 160.

Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.

Gutwin et al., "Gone But Not Forgotten: Designing for Disconnection in Synchronous Groupware", CSCW 2010, Feb. 6-10, 2010, Savannah, Georgia, USA., pp. 179-188.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.

Hasegawa et al., "On a Portable Memory Device for Physical Activities and Informations of Maternal Perception", Journal of Perinatal Medicine, 1988, vol. 16, No. 4, pp. 349-356.

Hawley et al., "Clinical Implementation of an Automated Medical Information Bus in an Intensive Care Unit", Proceedings of the Annual Symposium on Computer Application in Medical Care, Nov. 9, 1988, pp. 621-624.

Hayes-Roth et al., "Guardian: A Prototype Intelligent Agent for Intensive-Care Monitoring", Artificial Intelligence in Medicine, vol. 4, Dec. 31, 1992, pp. 165-185.

Hospira, GemStar® Pain Management Infusion System 9-084-PR1-2-2, <www.hospira.com/products/gemstar_painmanagement.aspx>, Jan. 28, 2010, pp. 1-2.

Huang et al., "Secure Identity-Based Data Sharing and Profile Matching for Mobile Healthcare Social Networks in Cloud Computing", vol. 6, Jul. 2018, pp. 36584-36594.

Introducing Abbott TQPM (Total Quality Pain Management), Abbott Laboratories, Abbott Park, IL, May 2000, pp. 1-4.

"Infusion Pump", Wikipedia.org, as last modified Mar. 27, 2014, in 3 pages, <https://web.archive.org/web/20140703024932/https://en.wikipedia.org/wiki/Infusion_pump>.

Isaka et al., "Control Strategies for Arterial Blood Pressure Regulation", IEEE Transactions on Biomedical Engineering, Apr. 1993, vol. 40, No. 4, pp. 353-363.

Johnson et al., "Using BCMA Software to Improve Patient Safety In Veterans Administration Medical Centers", Journal of Healthcare Information Management, Dec. 6, 2004, vol. 16, No. 1, pp. 46-51.

Kent Displays, "Reflex™ Electronic Skins", Product Brief 25127B, 2009, pp. 2.

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

(56) References Cited

OTHER PUBLICATIONS

Li et al., "Hijacking an Insulin Pump: Security Attacks and Defenses for a Diabetes Therapy System", 2011 IEEE 13th International Conference on e-Health Networking, Applications and Services, 2011, pp. 150-156.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
"McKesson Automation and ALARIS Medical Systems Developing Point-of-Care Bar Coding Solution to Improve IV Medication Safety", PR Newswire, NY, Dec. 9, 2002, pp. 4.
Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Michienzi, Kelly, "Managing Drug Library Updates", Pharmacy Purchasing Products, https://www.pppmag.com/article/1061, Feb. 2012, vol. 9, pp. 22-23.
Micrel Medical Devices, "MP Daily +" <http://web.archive.org/web/20130803235715/http://www.micrelmed.com/index.aspx?productid=9> as archived Aug. 3, 2013 in 1 page.
Moghissi, Etie, Md, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nojoumian et al., "Social Secret Sharing in Cloud Computing Using a New Trust Function", 2012 Tenth Annual International Conference on Privacy, Security and Trust, pp. 161-167.
Nolan et al., "The P1073 Medical Information Bus Standard: Overview and Benefits for Clinical Users", 1990, pp. 216-219.
Omnilink Systems, Inc., "Portable Medical Equipment Tracking", <http://www.omnilink.com/portablemedicalequipmenttracking/>, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, <http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2>, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", May 15, 2008, pp. 63. <https://usme.com/content/manuals/sigma-spectrum-operator-manual.pdf>.
"Sigma Spectrum: Operator's Manual", Oct. 2009, pp. 72. <http://static.medonecapital.com/manuals/userManuals/Sigma-Spectrum-Operator-Manual-October-2009.pdf>.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.
Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.
Smith, Joe, "Infusion Pump Informatics", CatalyzeCare: Transforming Healthcare, as printed May 12, 2011, pp. 2.

(56) References Cited

OTHER PUBLICATIONS

Sodders, Lisa, "VA Center Keeps Medicine in Right Hands", The Capital-Journal, Dec. 4, 1999, pp. 1-2.
"Software Versioning", Wikipedia.org, dated Oct. 16, 2011 in 11 pages, <https://en.wikipedia.org/w/index.php?title=Software_versioning&oldid=455859110>.
Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
"TCG TPM v2.0 Provisioning Guidance", Reference, Version 1, Revision 1, Mar. 15, 2017, pp. 1-43.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yoo et al., "Code-Based Authentication Scheme for Lightweight Integrity Checking of Smart Vehicles", IEEE Access, 2018, vol. 6, pp. 46731-46741.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
International Search Report and Written Opinion received in PCT Application No. PCT/US2019/041706, dated Nov. 5, 2019 in 15 pages.
International Preliminary Report on Patentability and Written Opinion received in PCT Application No. PCT/US2019/041706, dated Jun. 11, 2020 in 6 pages.

* cited by examiner

TAGGING PUMP MESSAGES WITH IDENTIFIERS THAT FACILITATE RESTRUCTURING

INCORPORATION BY REFERENCE TO ANY PRIORITY APPLICATIONS

This application is a continuation of U.S. patent application Ser. No. 17/447,560, filed Sep. 13, 2021 and titled "TAGGING PUMP MESSAGES WITH IDENTIFIERS THAT FACILITATE RESTRUCTURING," which is a continuation of U.S. patent application Ser. No. 16/914,147, filed Jun. 26, 2020 and titled "TAGGING PUMP MESSAGES WITH IDENTIFIERS THAT FACILITATE RESTRUCTURING," which is a continuation of U.S. patent application Ser. No. 16/512,308, filed Jul. 15, 2019 and titled "TAGGING PUMP MESSAGES WITH IDENTIFIERS THAT FACILITATE RESTRUCTURING," which is a continuation of International Application No. PCT/US19/41706, filed Jul. 12, 2019 and titled "SYSTEMS AND METHODS FOR FACILITATING CLINICAL MESSAGING IN A NETWORK ENVIRONMENT," which claims priority to U.S. Provisional Application No. 62/699,499, filed on Jul. 17, 2018 and titled "SYSTEMS AND METHODS FOR FACILITATING CLINICAL MESSAGING IN A NETWORK ENVIRONMENT." Any and all applications for which a foreign or domestic priority claim is identified in the Application Data Sheet as filed with the present application are hereby incorporated herein by reference in their entirety under 37 CFR 1.57.

TECHNICAL FIELD

This disclosure relates to the field of clinical messaging, and particularly to techniques for facilitating clinical messaging within and across various network environments.

BACKGROUND

Modern medical care often involves the use of medical infusion pumps to deliver fluids and/or fluid medicine to patients. Infusion pumps permit the controlled delivery of fluids to a patient and provide flexible yet controlled delivery schedules. Infusion pumps can communicate with a server configured to manage the infusion statuses of the individual infusion pumps.

SUMMARY

Various techniques for facilitating communication with and across a clinical environment and a cloud environment are described herein. These techniques may include converting pump messages into standardized dataset messages (also referred to herein simply as "messages"), merging the messages into a cache, transmitting the messages to a cloud server, detecting network outages, clearing an outbound queue, detecting missing messages, authenticating a connectivity adapter for cloud access, providing a segmented data structure, among others. These and other embodiments are described in greater detail below with reference to FIGS. 1-13. Although many of the examples are described in the context of a hospital environment including infusion pumps, the techniques described herein can be applied to any network environment including other medical devices (e.g., patient care monitors configured to display blood pressure, heart rate, blood oxygenation, and the like), or non-medical devices, or any combination thereof.

BRIEF DESCRIPTION OF THE DRAWINGS

The embodiments described herein are illustrated by way of example, and not by way of limitation, in the figures of the accompanying drawings in which like references indicate similar elements.

DETAILED DESCRIPTION

Overview of Example Network Environment

Figure 1:
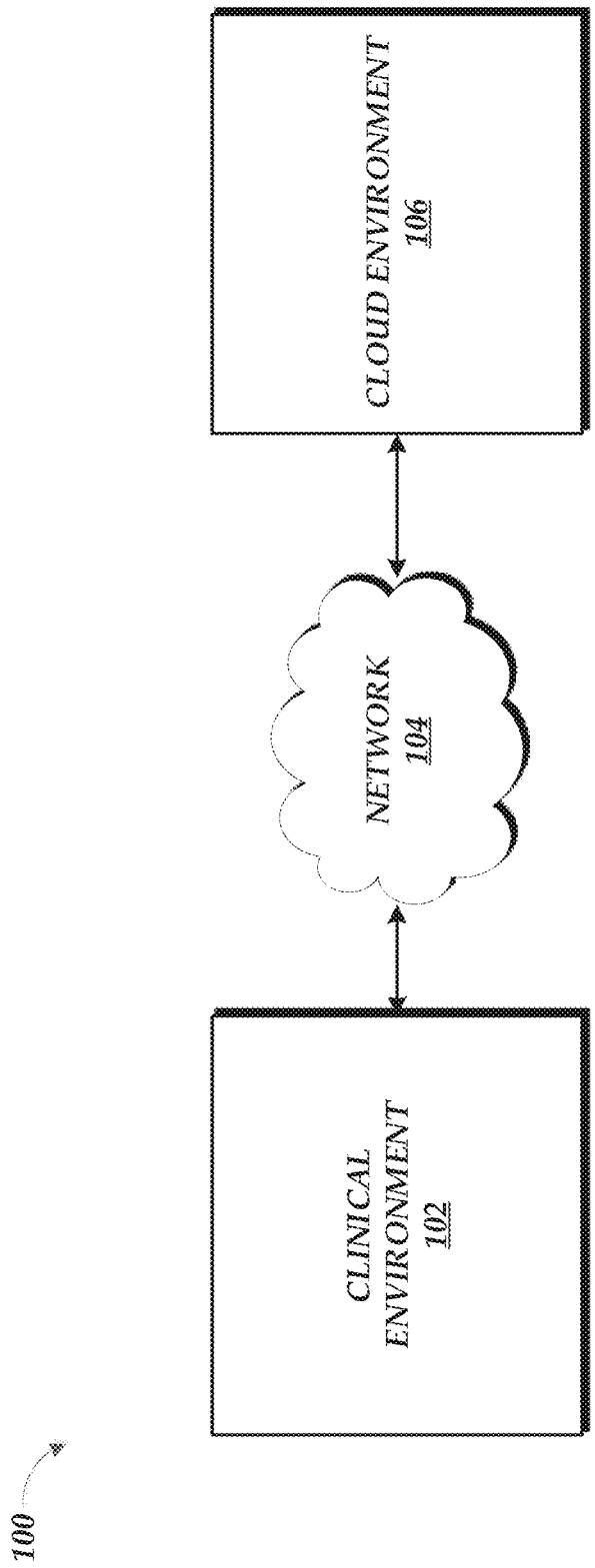
FIG. 1 is a block diagram of an example clinical environment and an example cloud environment in accordance with aspects of the present disclosure.

FIG. 1 illustrates network environment 100 in which clinical environment 102 communicates with cloud environment 106 via network 104. The clinical environment 102 may include one or more healthcare facilities (e.g., hospitals). The components of the clinical environment 102 are described in greater detail below with reference to FIG. 2. The network 104 may be any wired network, wireless network, or combination thereof. In addition, the network 104 may be a personal area network, local area network, wide area network, over-the-air broadcast network (e.g., for radio or television), cable network, satellite network, cellular telephone network, or combination thereof. For example, the network 104 may be a publicly accessible network of linked networks such as the Internet. For example, the clinical environment 102 and the cloud environment 106 may each be implemented on one or more wired and/or wireless private networks, and the network 104 may be a public network (e.g., the Internet) via which the clinical environment 102 and the cloud environment 106 communicate with each other. The cloud environment 106 may be a cloud-based platform configured to communicate with multiple clinical environments. The cloud environment 106 may include a collection of services, which are delivered via the network 104 as web services. The components of the cloud environment 106 are described in greater detail below with reference to FIG. 4.

Components of Clinical Environment

Figure 2:
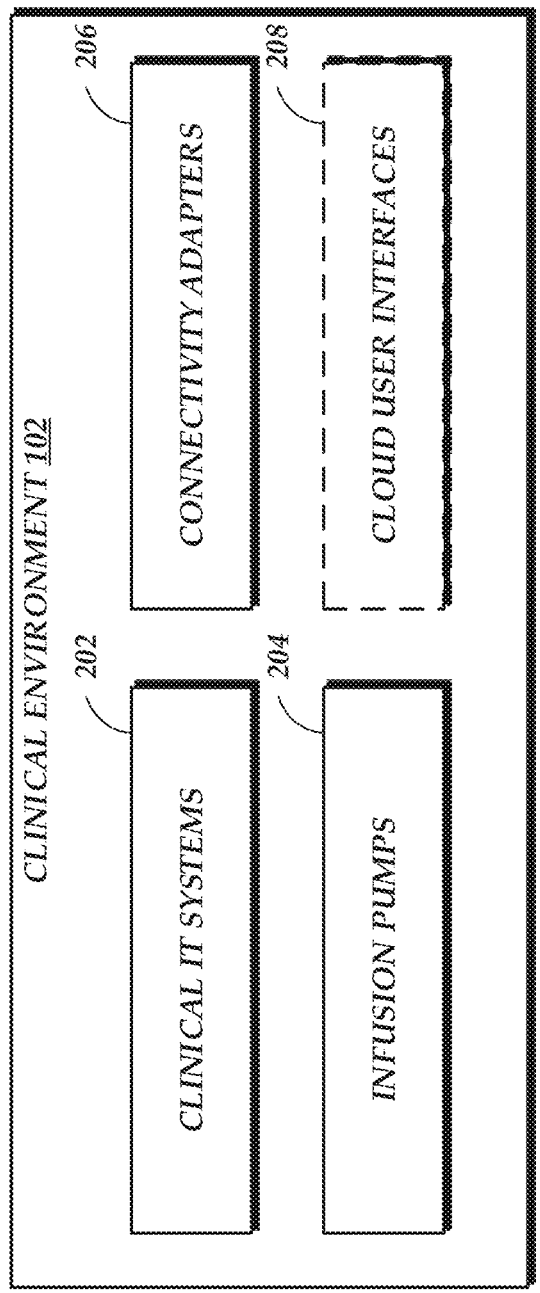
FIG. 2 is a block diagram illustrating components of a clinical environment in accordance with aspects of the present disclosure.

FIG. 2 illustrates the clinical environment 102, which includes one or more clinical IT systems 202, one or more infusion pumps 204, and one or more connectivity adapters 206. Further, the clinical environment 102 may be configured to provide cloud user interfaces 208 (e.g., generated and provided by the cloud environment 106). The clinical IT system 202 may include a hospital infusion system (HIS) designed to manage the facilities' operation, such as medical, administrative, financial, and legal issues and the corresponding processing of services. The HIS can include one or more electronic medical record (EMR) or electronic health record (EHR) systems, as well. The infusion pump 204 is a medical device configured to deliver medication to a patient. The connectivity adapter 206 is a network component configured to communicate with other components of the clinical environment 102 and also communicate with the cloud environment 106 on behalf of the other components of the clinical environment 102. In one embodiment, all messages communicated between the clinical environment 102 and the cloud environment 106 pass through the connectivity adapter 206. In some cases, the connectivity adapter 206 is a network appliance with limited storage space (e.g., memory and/or persistent storage). The cloud user interfaces 208 may be provided to a user in the clinical environment 102 via a browser application, desktop application, mobile application, and the like. The user may access status reports and other data stored in the cloud environment 106 via the cloud user interfaces 208.

The components 202-208 illustrated in FIG. 2 may communicate with one or more of the other components in the clinical environment 102. For example, each of the clinical IT system 202 and the infusion pump 204 may communicate with the connectivity adapter 206 via physical local area network (LAN) and/or virtual LAN (VLAN). Although not shown in FIG. 2, the clinical environment 102 may include other medical devices and non-medical devices that facilitate the operation of the clinical environment 102.

Overview of Messaging in the Clinical Environment

Figure 3:
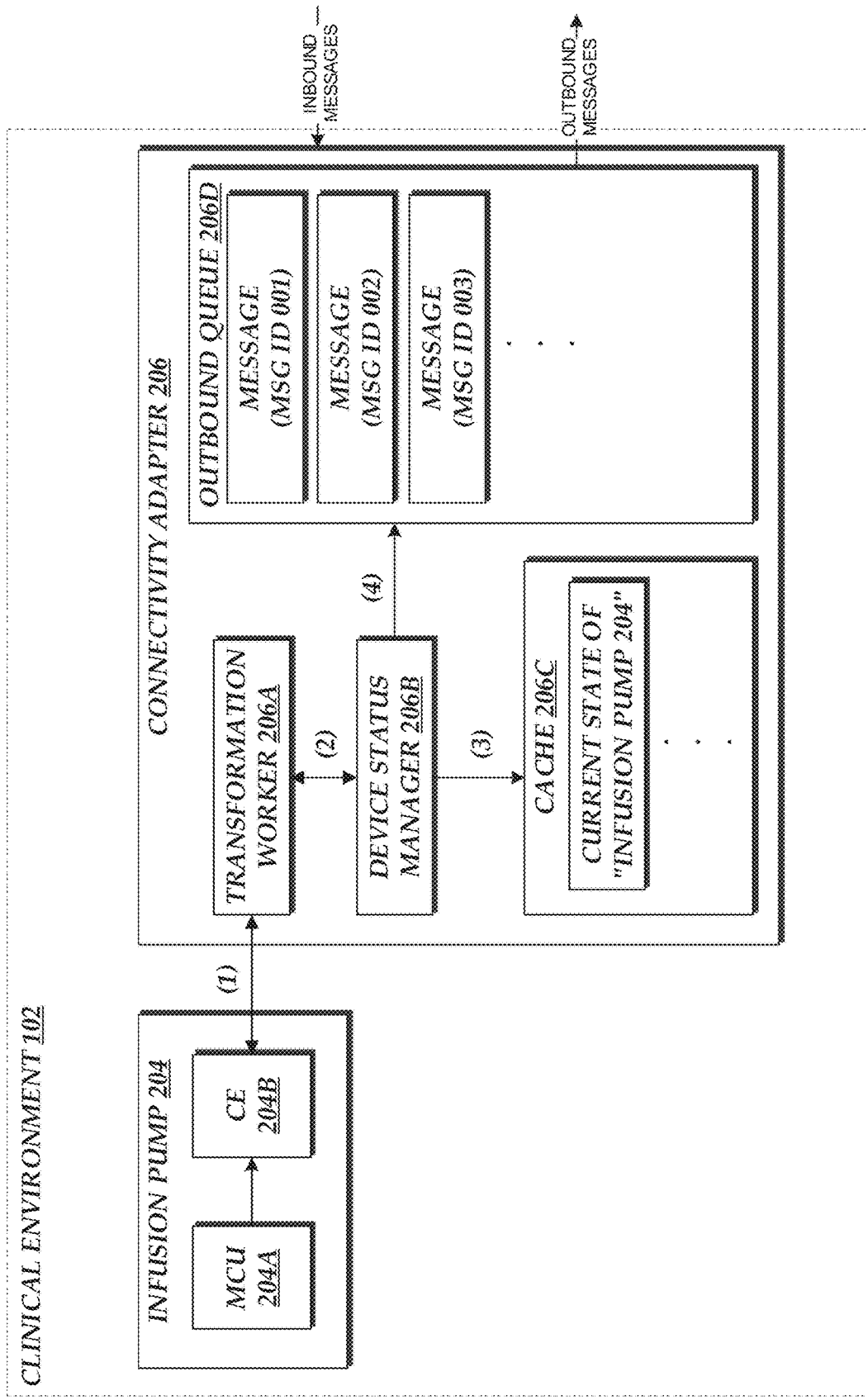
FIG. 3 is a schematic diagram illustrating components of an infusion pump and a connectivity adapter of a clinical environment in accordance with aspects of the present disclosure.

FIG. 3 illustrates the messages received, stored, and transmitted by the connectivity adapter 206 in the clinical environment 102. As shown in FIG. 3, the infusion pump 204 may include motor controller unit (MCU) 204A and communications engine (CE) 204B. Although not shown in FIG. 3, the infusion pump 204 may include one or more memories and storage media configured to store various instructions, parameters, and/or messages. The connectivity adapter 206 may include transformation worker 206A, device status manager 206B, cache 206C, and outbound queue 206D. The MCU 204A may generate and send messages to the CE 204B for storage and transmission to the connectivity adapter 206. In some cases, the messages are each associated with a message identifier (ID). In some embodiments, the MCU 204A is a very small processor (e.g., 12 Mhz) and the CE 204B is a more powerful processor (e.g., 400 Mhz). Pump messages sent to the connectivity adapter 206 generated by the MCU 204A may be transformed into a standardized dataset message (e.g., message format used by the connectivity adapter 206 to communicate with the cloud environment 106, also referred to herein simply as "messages"). In some embodiments, the standardized dataset format may allow multiple messages to be merged into a single standard dataset message that includes all the information included in the multiple messages. For example, a pump message that indicates the start of an infusion and another pump message that indicates the presence of an air-in-line alarm may occupy different locations within the standardized dataset message. Even though the start-of-infusion message was generated long before the air-in-line-alert message, they may be transmitted together packaged in the standardized dataset message without having to worry about having incomplete information about the infusion pump 204 at any given moment or having to request older messages that have been lost or become unavailable. The device status manager 206B processes the transformed messages provided by the transformation worker 206A and merges the data included in the transformed messages into the cache 206C, which represents the current state of the infusion pump 204. For example, the cache 206C may include all of the current parameter values (or to the extent available to the connectivity adapter 206) at the infusion pumps connected to the connectivity adapter 206 (e.g., power status, infusion status, battery status, network status, infusion start time, volume to be infused, volume infused, dose, and the like). Although not shown in FIG. 3, the clinical IT system 202 may maintain the identities of the patients assigned to the individual infusion pumps 204 and other data that the connectivity adapter 206 may utilize in order to merge the messages from the pump into the cache 206C. For example, the client IT system 202 may send instructions for programming the infusion pump 204 for initiating an infusion on a patient, and the instructions may include identifiers such as an infusion ID and a patient ID. Upon receiving a pump message containing the infusion ID, the connectivity adapter 206 can use the infusion ID to determine that the pump message relates to the patient having the patient ID (even when the pump message does not include the patient ID) based on the prior instructions received from the client IT system 202. The connectivity adapter 206 can then add the information included in the pump message to the cache 206C along with the patient ID.

The device status manager 206B also sends the transformed messages to the outbound queue 206D for transmission to the cloud environment 106. The messages stored in the outbound queue 206D may be associated with one or more message IDs. For example, a message can be associated with a single message ID corresponding to the original pump message. In another example, a message can include data from multiple pump messages and therefore include multiple message IDs. The messages transmitted from the outbound queue 206D to the cloud environment 106 may be stored in the cloud environment 106 for providing reports and other data to a client (e.g., via the cloud user interfaces 208) and/or for compliance purposes. Additional details regarding the messaging in the clinical environment 102 are provided below.

Components of Cloud Environment

Figure 4:
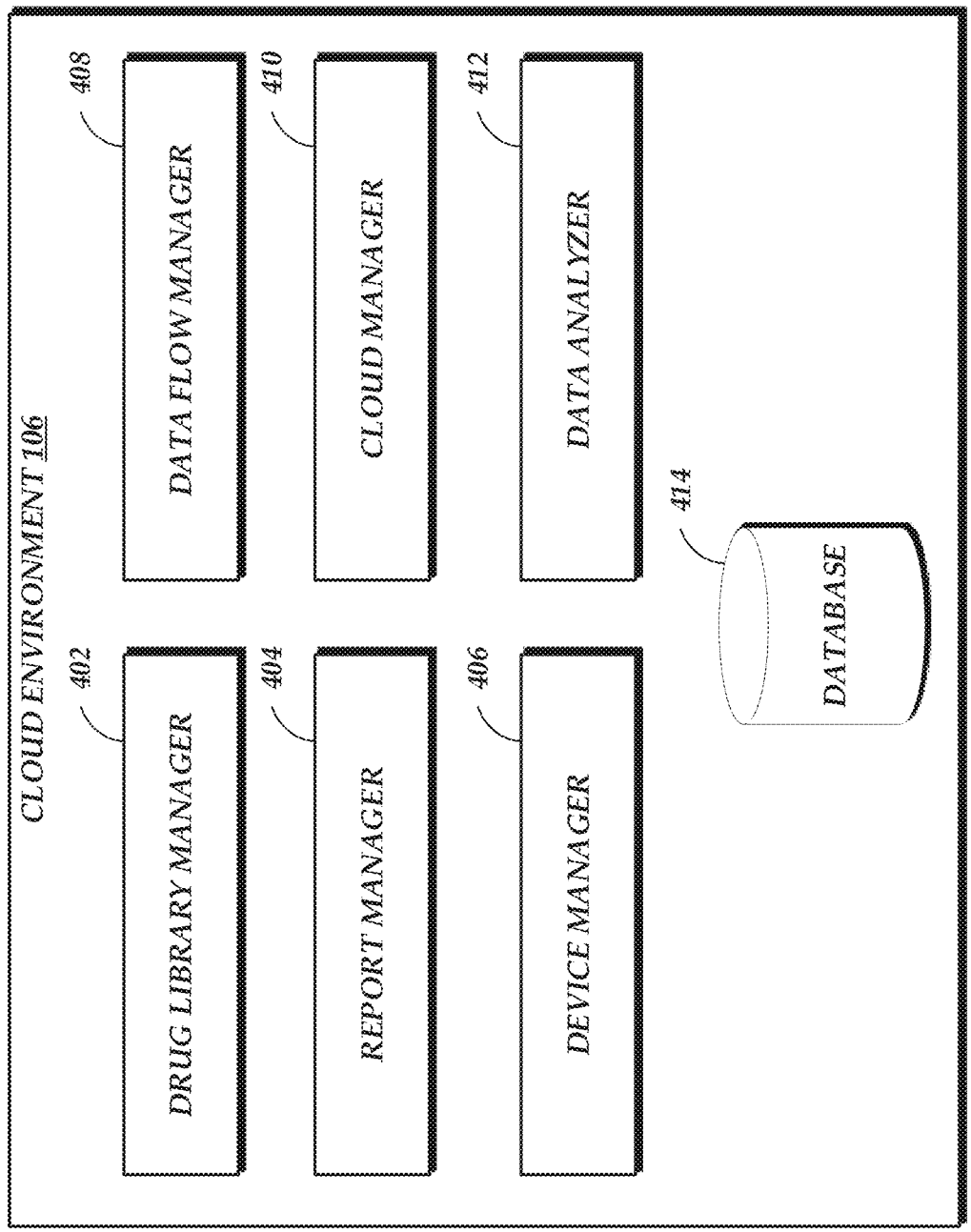
FIG. 4 is a block diagram illustrating components of a cloud environment in accordance with aspects of the present disclosure.

FIG. 4 illustrates the cloud environment 106, which includes drug library manager (DLM) 402, report manager 404, device manager 406, data flow manager (DFM) 408, cloud manager (CM) 410, data analyzer (DA) 412, and database 414.

The DLM 402 may provide a set of features and functions involved in the creation and management of drug libraries for use with infusion pumps. These drug libraries may provide user-defined settings for pump configuration and drug infusion error reduction.

The report manager 404 may provide various reporting capabilities for clinically relevant infusion data which users can choose to use for further analysis, such as tracking and trending of clinical practices.

The device manager 406 may oversee and manage the maintenance of infusion pumps, providing users the capability to view and manage asset and operational data. For example, the device manager 406 may schedule drug library and software updates for infusion pumps.

The DFM 408 may facilitate storing, caching, and routing of data between compatible infusion pumps 204, connectivity adapters 206, cloud services (e.g., infusion pump management software including modules 402-414 of FIG. 4), and external systems. For example, the DFM may store infusion and operational data received from infusion pumps, store and cache infusion pump drug libraries and software images, convert and route network messaging between the cloud environment 106 and the clinical environment 102, convert and route medication order information from a hospital information system to an infusion pump (e.g., auto-programming or smart-pump programming), and/or convert and route alert information and infusion events from infusion pumps to hospital information systems (e.g., alarm/alert forwarding, and auto-documentation, or infusion documentation).

The CM 410 may serve as a general-purpose computing platform for the other modules illustrated in FIG. 4. Functionally, the CM 410 may be similar to Microsoft Windows® or Linux® operating systems as it provides the following services: networking, computation, user administration and security, storage, and monitoring.

The DA 412 may provide data analytics tools for generating user interfaces and reports based on the data generated and/or received by the other modules illustrated in FIG. 4.

The database 414 may store data generated and/or received by the modules 402-412 of the cloud environment 106. Although not illustrated in FIG. 4, the cloud environment may provide other resources such as processors, memory, disk space, network, etc. The modules 402-412 may be hardware components configured to perform one or more of the techniques described herein. Alternatively, the modules 402-412 may be implemented using software instructions stored in physical storage and executed by one or more processors. Although illustrated as separate components, the modules 402-412 may be implemented as one or more hardware components (e.g., a single component, individual components, or any number of components), one or more software components (e.g., a single component, individual components, or any number of components), or any combination thereof.

In some embodiments, the cloud environment 106 can be implemented using a commercial cloud services provider (e.g., Amazon Web Services®, Microsoft Azure®, Google Cloud®, and the like). In other embodiments, the cloud environment can be implemented using network infrastructure managed by the provider and/or developer of the modules 402-412 shown in FIG. 4. In some embodiments, the features and services provided by one or more of the modules 402-412 may be implemented on one or more hardware computing devices as web services consumable via one or more communication networks. In further embodiments, one or more of the modules 402-412 are provided by one or more virtual machines implemented in a hosted computing environment. The hosted computing environment may include one or more rapidly provisioned and released computing resources, such as computing devices, networking devices, and/or storage devices.

Overview of Messaging in the Cloud Environment

Figure 5:
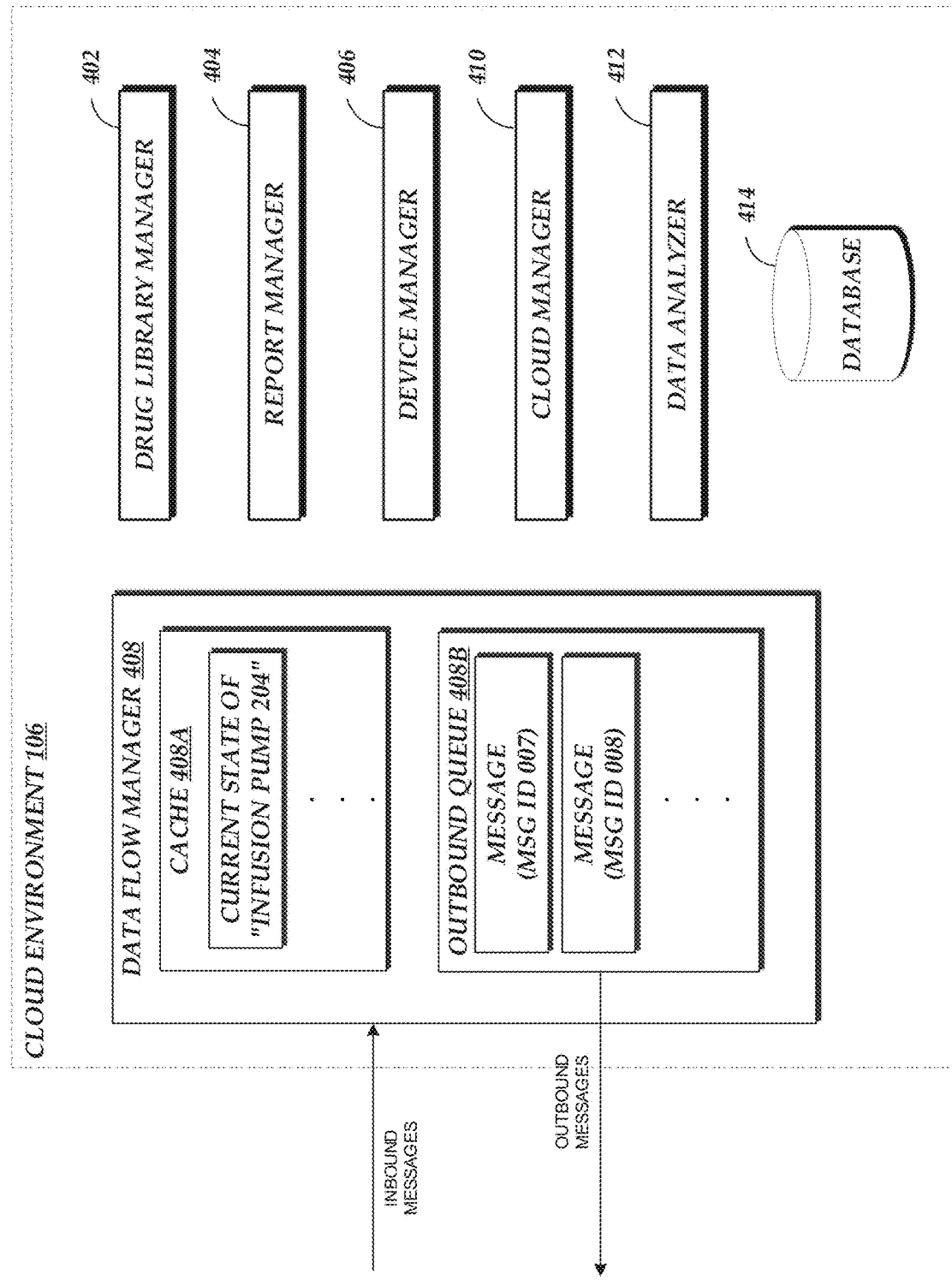
FIG. 5 is a schematic diagram illustrating components of a data flow manager of a cloud environment in accordance with aspects of the present disclosure.

FIG. 5 illustrates the messages received, stored, and transmitted by the cloud environment 106. As shown in FIG. 5, the DFM 408 may include cache 408A and outbound queue 408B. The cache 408A may store the current state of the infusion pump 204. For example, the cache 408A may include all of the current parameter values (or to the extent available to the DFM 408) at the infusion pump 204 (e.g., power status, infusion status, battery status, network status, infusion start time, volume to be infused, volume infused, dose, and the like). In some cases, the current state stored in the cache 408A is identical to the current state stored in the cache 206C. In other cases, the current state stored in the cache 408A includes additional information not stored in the cache 206C, or vice versa. For example, the DFM 408 may have access to data sources not accessible (or readily accessible) by the connectivity adapter 206, and the DFM 408 may have obtained additional data prior to merging the message and the additional data into the cache 408A. In another example, due to a network outage, the connectivity adapter 206 may have been able to update its own cache 206C but unable to transmit the relevant messages to the DFM 408. In such a case, the cloud cache 408A may include less information than the connectivity adapter cache 206C. The outbound queue 408B may include messages to be transmitted to the clinical environment 102. For example, the outbound queue 408B can include command messages (e.g., instructions to update the security settings on the connectivity adapter 206), request messages (e.g., requests for missing messages for logging purposes), etc. In other examples, the outbound queue 408B may include log requests, drug library updates, software updates, security updates, and the like. In some embodiments, the items in the outbound queue 408B are less time-sensitive than the items in the outbound queue 206D. The process of detecting and requesting missing messages from the clinical environment 102 is described in greater detail below with reference to FIG. 7. In some cases, the data stored in the cache 408A may be copied or moved to the database 414.

Generation and Transmission of Pump Messages

Referring back to FIG. 3, when there is an event at the infusion pump 204 (e.g., the device has been powered on, infusion has been started or finished, an alarm condition has been satisfied, etc.), the MCU 204A generates a message indicative of such an event and transmits the message to the CE 204B. Upon receiving one or more messages from the MCU 204A, the CE 204B packages the messages received so far into a pump message (e.g., according to a protocol specific to the infusion pump 204) and transmits the pump message to the connectivity adapter 206. For example, if multiple messages have been received from the MCU 204A since the most recent pump message transmitted to the connectivity adapter 206, the CE 204B may merge the information included in the multiple messages into a single pump message in accordance with the pump protocol. The pump message transmitted to the connectivity adapter 206 may be reflective of the current state of the infusion pump 204 at the time the pump message is transmitted to the connectivity adapter 206. In some embodiments, the infusion pumps 204 do not have Internet access and communicate only with the connectivity adapter 206 (e.g., to ensure that Internet connection is not needed for any clinical operations). In other embodiments, the infusion pumps 204 may communicate with network entities other than the connectivity adapter 206 (e.g., the cloud environment 106 via the Internet).

The infusion pump 204 may store its current and prior states (e.g., days, months, or years of messages received from the MCU 204A or transmitted by the CE 204B) in data store (not shown) located within the infusion pump 204. As discussed further below, the connectivity adapter 206 may process requests from the DFM 408 for pump messages. For example, the DFM 408 may request messages from the infusion pump 204 when the DFM 408 realizes that it is missing one or more pump message. Pump messages can be missed by the DFM 408 during network outages, or other disruptions to network traffic. In such situations, as will be discussed in greater detail below, the DFM 408 can request the missing pump messages from the connectivity adapter 206. The messages from the infusion pump 204 may include one or more parameters. Some of those parameters may be data fields that are overwritten as the parameters are updated. Other parameters are linked lists that include a sequence of past parameter values. For example, fields may be used for statuses such as power status, infusion status, and the like, and linked lists may be used for alerts, ruleset violations, and the like.

Connecting Infusion Pumps to Connectivity Adapter

In the event that the connection between the infusion pump 204 and the connectivity adapter 206 is terminated or otherwise unavailable, the MCU 204A may continue to generate messages and the CE 204B may continue to merge such additional messages into the most current state of the infusion pump 204. Once the connection between the infusion pump 204 and the connectivity adapter 206 is re-established, the CE 204B may transmit a single pump message (or multiple pump messages) that reflects all of the messages received from the MCU 204A during the time of lost connectivity. For example, if the CE 204B, during the time of lost connectivity, received a message that indicates that the power status changed to "on" and subsequently received another message that indicates that the infusion status changed to "on," the CE 204B may generate a pump message that has two key-value pairs, "power status=on" and "infusion status=on." In other cases, these messages may be transmitted to the connectivity adapter 206 as separate pump messages.

In some embodiments, when the infusion pump 204 is turned on after being off for a period of time, or upon the connection between the infusion pump 204 and the connectivity adapter 206 being re-established, the infusion pump 204 sends all of the available, unsent messages or data to the connectivity adapter 206. In some cases, such an approach may overload the internal network of the clinical environment 102 (e.g., if 500 infusion pumps 204 came back online after being offline for weeks). Thus, in some cases, the connectivity adapter 206 may deliberately reject such pump messages to reduce the network load, and have the infusion pumps 204 re-send the pump messages at a later time. The infusion pumps 204 may adopt a schedule for re-sending rejected pump messages that further reduces the network load (e.g., exponential back-offs where each retry is performed after a longer wait period, randomization where the back-offs are not strictly exponential and include random temporal variations, a combination of exponential back-offs and randomization, etc.).

By analyzing the pump messages received from the infusion pump 204, the connectivity adapter 206 may determine that it has missed one or more messages that it should have received (e.g., due to older data being overwritten in the pump message). For example, if the connectivity adapter 206 receives a pump message that indicates that the power state of the infusion pump 204 has gone from "sleep" to "on," where the information in the cache 206C indicates that the most recent power state of the infusion pump 204 was "on." By comparing the pump message and the information in the cache 206C, the connectivity adapter 206 can determine that it must have missed a pump message that indicates that the power state of the infusion pump 204 was changed from "on" to "sleep." In some cases, the connectivity adapter 206 requests these missing messages from the infusion pump 204 immediately. In other cases, the connectivity adapter 206 requests these missing messages at a later time (e.g., when the network activity is light or below a threshold). In some cases, the connectivity adapter 206 determines missing pump messages based on message IDs that are not in sequence. For example, pump messages may include message IDs that are sequential (such that one pump message generated immediately subsequently to another pump message has a message ID that immediately follows the message ID of said another message in a predetermined sequence of numbers or identifiers). In such a case, upon processing pump messages having message IDs 100050 and 100055 in a row, the connectivity adapter 206 may determine that pump messages having message IDs 100051-100054 were deleted, overwritten, or lost.

Transformation of Pump Messages

The transformation worker 206A receives the pump messages and converts it to a standardized message format (e.g., standardized dataset messages used for transmitting information within and across the clinical environment 102 and the cloud environment 106). In some embodiments, the standardized dataset message can be a collection or envelope of messages that are each a key-value pair. For example, the standardized dataset message may include one key-value pair that says "message ID=100015," another key-value pair that says "power status=on," and another key-value pair that says "volume to be infused=5 mL." In some cases, the standardized dataset message may include one or more keys having no value or having default values (e.g., "alarm count=0," or "battery status=unknown"). Depending on the pump protocol associated with the pump message, the same information may be located in different parts of the pump message. The transformation worker 206A identifies the data included in the pump messages based on the pump protocol and places the data into the appropriate locations of a standardized dataset message. For example, based on the pump protocol, the transformation worker 206A extracts the power state of the infusion pump 204 and places the power state information in the standardized dataset message, which also includes information other than the power state. For example, all parameters or key-value pairs in the standardized dataset message other than those specified by the pump message may be set to default values. In some cases, such parameters or key-value pairs are left blank. Similarly, when requests are sent to the infusion pump 204, the transformation worker 206A transforms the standardized dataset message into a pump message understood by the infusion pump 204. In some embodiments, the transformation worker 206A may be implemented using a ruleset engine. In one embodiment, using a ruleset engine advantageously does not require the transformation worker 206A to be rebooted when a new infusion pump or a new pump protocol is added. For example, the ability to be able to translate pump messages in a new pump protocol can be implemented as a configuration file that can be added to the connectivity adapter 206, where the configuration file allows the transformation worker 206A to be able to receive and process pump messages in the new pump protocol. Once the configuration file is added to the connectivity adapter 206, the transformation worker 206A can begin transforming such pump messages into the standardized dataset messages for further processing by the device status manager 206B. In some cases, if the transformation worker 206A does not recognize a pump message or the protocol used by the pump message or otherwise cannot process the pump message, the transformation worker 206A stores the pump message in the connectivity adapter 206 and transforms the pump message upon the transformation mapping for the pump protocol becoming available.

The transformation worker 206A may further include hints in the header of the standardized dataset message. The hints indicate to the device status manager 206B which portions of the standardized dataset message contain new information and should thus be accessed by the device status manager 206B and merged into the cache 206C. Based on the hints, the device status manager 206B can refrain from having to process the entire standardized dataset message generated by the transformation worker 206A. For example, the standardized dataset message may have a hierarchical tree structure having five categories of pump parameters, where each category includes multiple pump parameters or sub-categories having multiple parameters. If only a parameter in one of the categories includes new information, the transformation worker 206A may set a binary flag associated with that category to 1 and the binary flags associated with the remaining categories to 0 to indicate that the four categories do not include any new information. A given standardized dataset message may include a single hint indicating the location of the single piece of new information. Alternatively, the standardized dataset message may include multiple hints indicating the multiple locations where new information is provided.

Caching in Connectivity Adapter

The device status manager 206B takes the message received from the transformation worker 206A and "merges" the message into the cache 206C. Merging a message into the cache may include updating the data stored in the cache 206C based on the information included in the message. In some cases, the message may include information that prompts the device status manager 206B to access additional information from other databases or sources and adding such additional information to the cache 206C. For example, based on the infusion ID provided in the message, the device status manager 206B may access the identity of the patient associated with the infusion pump having the infusion ID and store that information in the cache 206C. As another example, the device status manager 206B may access the clinical IT system 202 or the cloud environment 106 for additional information that can be stored in the cache 206C. Accordingly, information from multiple data sources may be merged into the cache 206C in response to the pump messages received from the infusion pump 204. In yet another example, in the event that the information needed by the device status manager 206B is in the cloud environment 106 (e.g., the pump message references a drug library that is not yet stored in the clinical environment 102), the device status manager 206B merges the message into the cache 206C and places the message in the outbound queue 206D without accessing the cloud environment 106 (e.g., to make the message more complete based on the information in the cloud environment 106). In such a case, the DFM 408 may, upon receiving the message, access the necessary information, fill in the missing information in the message, and merge the message into the cache 408A. In some cases, the device status manager 206B may add information to the message (e.g., facility ID, account ID, etc.) before (or after) merging the message into the cache 206C.

The cache 206C may store the current state of the individual infusion pumps 204 configured to communicate with the connectivity adapter 206. As additional messages are received from the infusion pumps 204, the device status manager 206B updates the current state stored in the cache 206C to reflect the changes made by the messages from the infusion pumps 204. In some embodiments, the device status manager 206B determines whether the message received from the transformation worker 206A is a live message or an historical message. A live message includes messages that are transmitted to the connectivity adapter 206 based on a new event at the infusion pump 204. An historical message includes messages that are transmitted to the connectivity adapter 206 based on a prior event at the infusion pump 204. Historical messages may be transmitted at the request of the connectivity adapter 206. The device status manager 206B is configured to merge the message into the cache 206C upon determining that the message is a live message (and alternatively, refrain from merging the message into the cache 206C upon determining that the message is an historical message). The cache 206C may be implemented using an in-memory cache (e.g., Redis) or other storage devices.

In some cases, the messages sent to the cloud environment 106 are copies of the current state of the infusion pump 204 stored in the cache 206C at the time the messages are sent to the cloud environment 106. In other cases, the messages sent to the cloud environment 106 may not include all the parameters included in the current state of the infusion pump 204 stored in the cache 206C. For example, the messages sent to the cloud environment 106 only includes information that might not be stored in the cloud environment 106. In some cases, the device status manager 206B does not include in the message transmitted to the cloud environment 106 at least some of the information in the cache 206C if such information is otherwise available to the cloud environment 106. In another example, the message may include a log request, which is not intended to reflect the current state of an infusion pump. Such a log request may include a flag that indicates that the message is a log request and a parameter identifying the requested information.

Outbound Queues

Once a message has been merged into the cache 206C, the device status manager 206B adds the message to the outbound queue 206D for transmission to the cloud environment 106. In some embodiments, the device status manager adds the message to the outbound queue 206D regardless of whether the connectivity adapter 206 is connected to the cloud environment 106. The connectivity adapter 206 may include a separate outbound queue for transmitting messages to the clinical IT system 202.

The connectivity adapter 206 may include a service that picks up the messages stored in the outbound queue 206D and tries to route them to the appropriate endpoints. Such a service may determine whether the connectivity adapter 206 is connected to the cloud environment 106 or not. As will be further described below, such a service may determine whether the messages in the outbound queue 206D should be kept in the outbound queue 206D or removed from the outbound queue 206D.

Network Outages

The clinical environment 102 may be designed such that clinical functions of the clinical environment 102 continue to operate normally even during Internet outages or loss of connectivity to the cloud environment 106. Thus, in some embodiments, clinical functions do not rely on connectivity to the cloud environment 106 or information to be requested and received from the cloud environment 106. However, in some cases, the messages stored in the outbound queue 206D may be held in the outbound queue 206D (e.g., in the event of network jitter or momentary loss of connection) or removed from the outbound queue 206D (e.g., in the event of prolonged outage or after the outbound queue 206D becomes full) during an Internet or network outage.

For example, upon determining that the connection to the cloud environment 106 has been terminated or otherwise become unavailable, the connectivity adapter 206 may determine whether the outbound queue 206D includes any messages to be transmitted to the cloud environment 106 and discard one or more of the messages from the outbound queue 206D. For example, in the event of a prolonged outage, there may be a large number of messages in the outbound queue 206D, which may overload the network. For example, the large number of messages in the outbound queue 206D may delay transmission of time-sensitive alerts and may even include messages that are no longer relevant due to the length of the network outage. To prevent such issues, some of the messages in the outbound queue 206D may be removed without transmitting them to the cloud environment 106. In such cases, the cloud environment 106 will request those "missing" messages at a later time. In some embodiments, the messages in the outbound queue are discarded based on time (e.g., after being in the outbound queue for a specific amount of time). Alternatively, the determination of whether to discard one or more messages may be based on the size of the outbound queue. For example, the outbound queue may be fixed in size, and the oldest message is discarded upon a new message being added to the outbound queue that is full. For example, the messages may be discarded based on a first-in first-out (FIFO) manner. In some cases, the connectivity adapter 206 starts removing messages from the outbound queue 206D only after the outbound queue 206D reaches a threshold message size.

Outbound Queue Clearing Method

Figure 6:
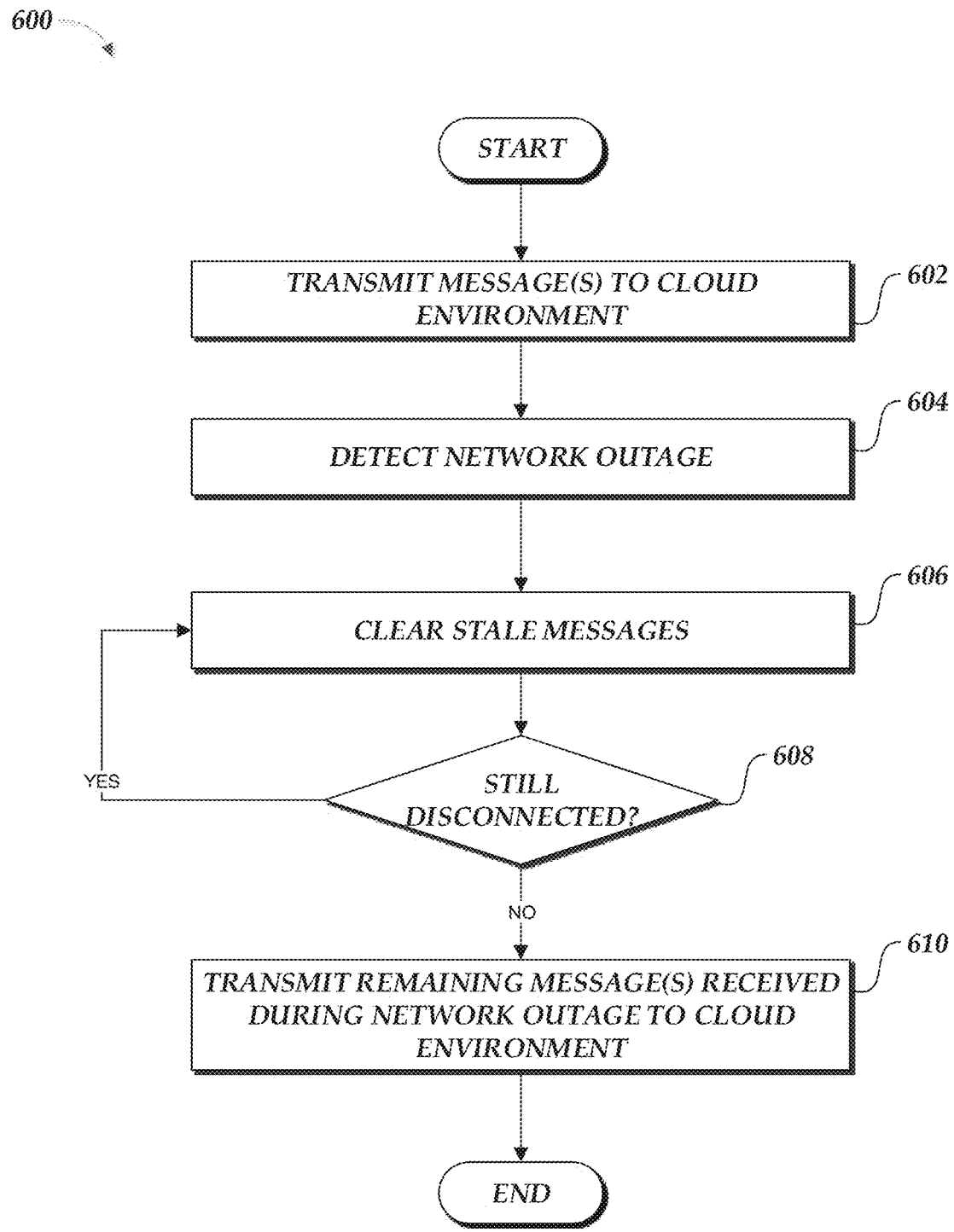
FIG. 6 is a flow diagram illustrating an example method for clearing an outbound queue in accordance with aspects of the present disclosure.

With reference now to FIG. 6, an example outbound queue clearing method 600 will be described. Since the connectivity adapter 206 does not have unlimited resources, during a network outage, the connectivity adapter 206 cannot let unsent messages pile up in the outbound queue 206D indefinitely. Further, as discussed above, having to send old messages that have been in the outbound queue 206D for a long time and no longer relevant may reduce network performance and interfere with transmission of messages that are more relevant. The example method 600 may be carried out, for example, by the connectivity adapter 206 of FIG. 3 (or one or more components thereof). The method 600 illustrates an example algorithm that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then executed by the CPU or microcontroller. For example, when the method 600 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. In some embodiments, the method 600 or portions thereof may be implemented on multiple processors, serially or in parallel. For convenience, the steps of the example method 600 are described as being performed by the connectivity adapter 206.

At block 602, the connectivity adapter 206 transmits one or more messages to the cloud environment 106. As discussed above, the transmitted messages may be processed by the DFM 408 in the cloud environment 106 and merged into the cloud cache 408A.

At block 604, the connectivity adapter 206 detects a network outage. For example, the connectivity adapter 206 may detect the outage based on not having received during a specific time window an acknowledgement of receipt of a message transmitted to the cloud environment 106. In some other cases, the connectivity adapter 206 may detect the outage based on its ping receiver not receiving any pings from the cloud environment 106 during a specific time window. In yet other cases, the connectivity adapter 206 may detect the outage based on receiving a message that the connection to the cloud environment 106 has been terminated. In some cases, the connectivity adapter 206 does not determine whether there is a network outage and tries to transmit a given message to the cloud environment 106 until an acknowledgement signal is received for the receipt of the given message. In such cases, the given message may remain in the outbound queue 206D until the message is successfully transmitted to the cloud environment 106 or otherwise removed from the outbound queue 206D (e.g., as discussed with reference to block 606).

At block 606, the connectivity adapter 206 clears stale messages from the outbound queue 206D. For example, stale messages may include messages associated with a pump event that is older than a threshold amount of time. In another example, stale messages may include messages that have been in the outbound queue 206D for more than a threshold amount of time. In some cases, the threshold amount of time may be pump-specific or pump-event-type-specific. For example, time-sensitive events may have a shorter threshold amount of time. In yet another example, a stale message may include a message that has been in the outbound queue 206D for the longest period of time (e.g., first in). In some cases, the connectivity adapter 206 may not clear or remove messages from the outbound queue 206D unless the outbound queue 206D is full.

At block 608, the connectivity adapter 206 determines whether the connectivity adapter 206 is connected to the cloud environment 106. Upon determining that the connectivity adapter 206 is not connected to the cloud environment 106, the connectivity adapter 206 proceeds to block 606 to clear any stale messages in the outbound queue 206D. Upon determining that the connectivity adapter 206 is connected to the cloud environment 106, the connectivity adapter 206 proceeds to block 610.

At block 610, the connectivity adapter 206 transmits any remaining messages received during the network outage and still stored in the outbound queue 206D (e.g., not deleted as stale).

In the method 600, one or more of the blocks shown in FIG. 6 may be removed (e.g., not performed) and/or the order in which the method 600 is performed may be switched. In some embodiments, additional blocks may be added to the method 600. The embodiments of the present disclosure are not limited to or by the example shown in FIG. 6, and other variations may be implemented without departing from the spirit of this disclosure.

Missing Messages

In some embodiments, each message generated by the MCU 204A is associated with a unique message ID. In other embodiments, each pump message generated by the CE 204B is associated with a unique message ID. In yet other embodiments, each standardized dataset message generated by the transformation worker is associated with a unique message ID. These message IDs may follow a predetermined sequence, and based on one or more combinations of these message IDs, the DFM 408 processing the messages from the connectivity adapter 206 may determine whether one or more messages are missing (e.g., have been generated but not received by the DFM 408). For example, upon determining that a message having a message ID of 10010 was immediately followed by a message having a message ID of 10016, the DFM 408 may determine that messages having message IDs 10011-10015 were not received and therefore missing. In some cases, the DFM 408 may be aware of periodic or scheduled messages expected to be received from the connectivity adapter 206. Upon determining that such messages were not received according to the schedule, the DFM 408 may request such messages from the connectivity adapter 206.

Upon determining that the DFM 408 is missing one or more events or messages, the DFM 408 may generate a request for such messages and store the request in the outbound queue 408B for transmission to the connectivity adapter 206. In some embodiments, the request is in the standardized dataset format and includes a flag having a value indicating that the request is a log retrieval request and not live data. A single log retrieval request may identify multiple messages to be requested from the infusion pump 204. Upon receiving the log retrieval requests from the cloud environment 106, the connectivity adapter 206 may transform the requests to one or more messages in the pump protocol and send to the infusion pump 204. Alternatively, the connectivity adapter 206 may throttle the requests based on the network load or condition of the clinical environment 102.

Missing Message Detection Method

Figure 7:
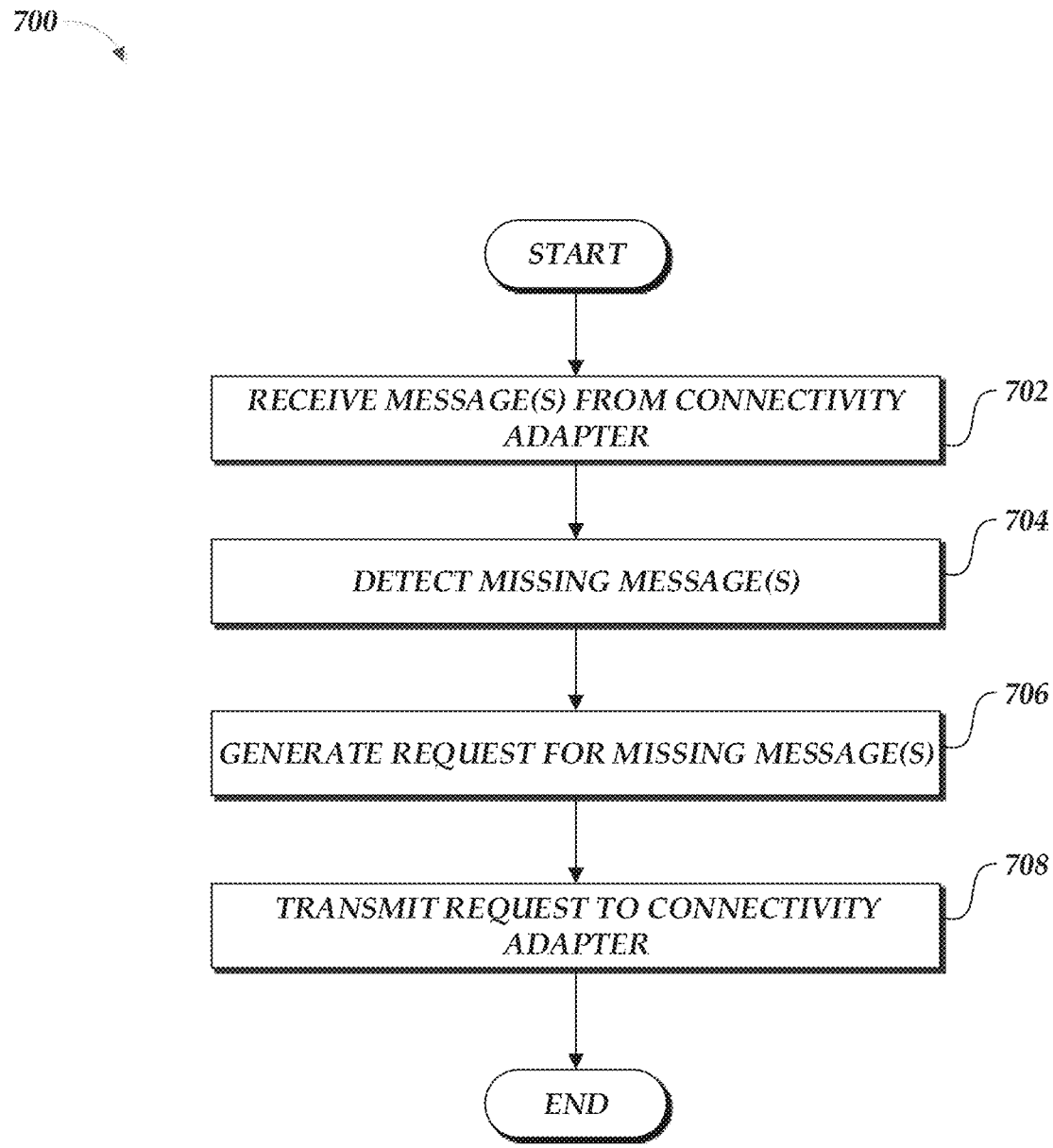
FIG. 7 is a flow diagram illustrating an example method for detecting missing messages in accordance with aspects of the present disclosure.

With reference now to FIG. 7, an example missing message detection method 700 will be described. The example method 700 may be carried out, for example, by the DFM 408 of FIG. 5 (or one or more components thereof). The method 700 illustrates an example algorithm that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then executed by the CPU or microcontroller.

For example, when the method 700 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. In some embodiments, the method 700 or portions thereof may be implemented on multiple processors, serially or in parallel. For convenience, the steps of the example method 700 are described as being performed by the DFM 408.

At block 702, the DFM 408 receives messages from the connectivity adapter 206. As discussed above, the messages may reflect the current state of the infusion pumps 204 connected to the connectivity adapter 206 and may be in the standardized dataset format.

At block 704, the DFM 408 detects missing messages. For example, the DFM 408 may detect one or more missing messages based on missing message IDs (i.e. after receiving a message with a message ID that does not immediately follow the message ID of the immediately prior message).

At block 706, the DFM 408 generates a request for the missing messages for transmission to the connectivity adapter 206. For example, the DFM 408 may wait until the number of missing messages reaches a threshold number (e.g., for a single pump or for a single connectivity adapter), and request the missing messages in bulk (e.g., under a single request). The generated request may be added to the outbound queue 408B.

At block 708, the DFM 408 transmits the request to the connectivity adapter 206. Upon receiving the request, the connectivity adapter 206 may generate a corresponding request for the requested messages for transmission to the infusion pump 204.

In the method 700, one or more of the blocks shown in FIG. 7 may be removed (e.g., not performed) and/or the order in which the method 700 is performed may be switched. In some embodiments, additional blocks may be added to the method 700. The embodiments of the present disclosure are not limited to or by the example shown in FIG. 7, and other variations may be implemented without departing from the spirit of this disclosure.

Merging Messages into Cloud Cache

The DFM 408 may merge the messages received from the connectivity adapter 206 into the cache 408A. In some cases, the DFM 408 merges a message into the cache 408A upon determining that the current time is within a threshold time period from the time associated with the message. For example, the DFM 408 may determine that a message associated with an alert generated 5 hours ago was received too late for the message to be merged into the cache 408A and refrain from merging the message into the cache 408A. In some embodiments, all data stored in the cloud cache 408A are received from the connectivity adapter 206, and the cloud cache 408A does not include any data that is not in the connectivity adapter 206 or was not previously processed by the connectivity adapter 206. In other embodiments, the cloud cache 408A stores drug library information, software update information, and the like that may not be in the connectivity adapter cache 206C. In some embodiments, the DFM 408 pre-processes a portion of the data stored in the cache 408A and/or pre-generates user interface data that may be requested by the clinical environment 102 and stores them in the cache 408A for faster access.

Message Merging and Caching Method

Figure 8:
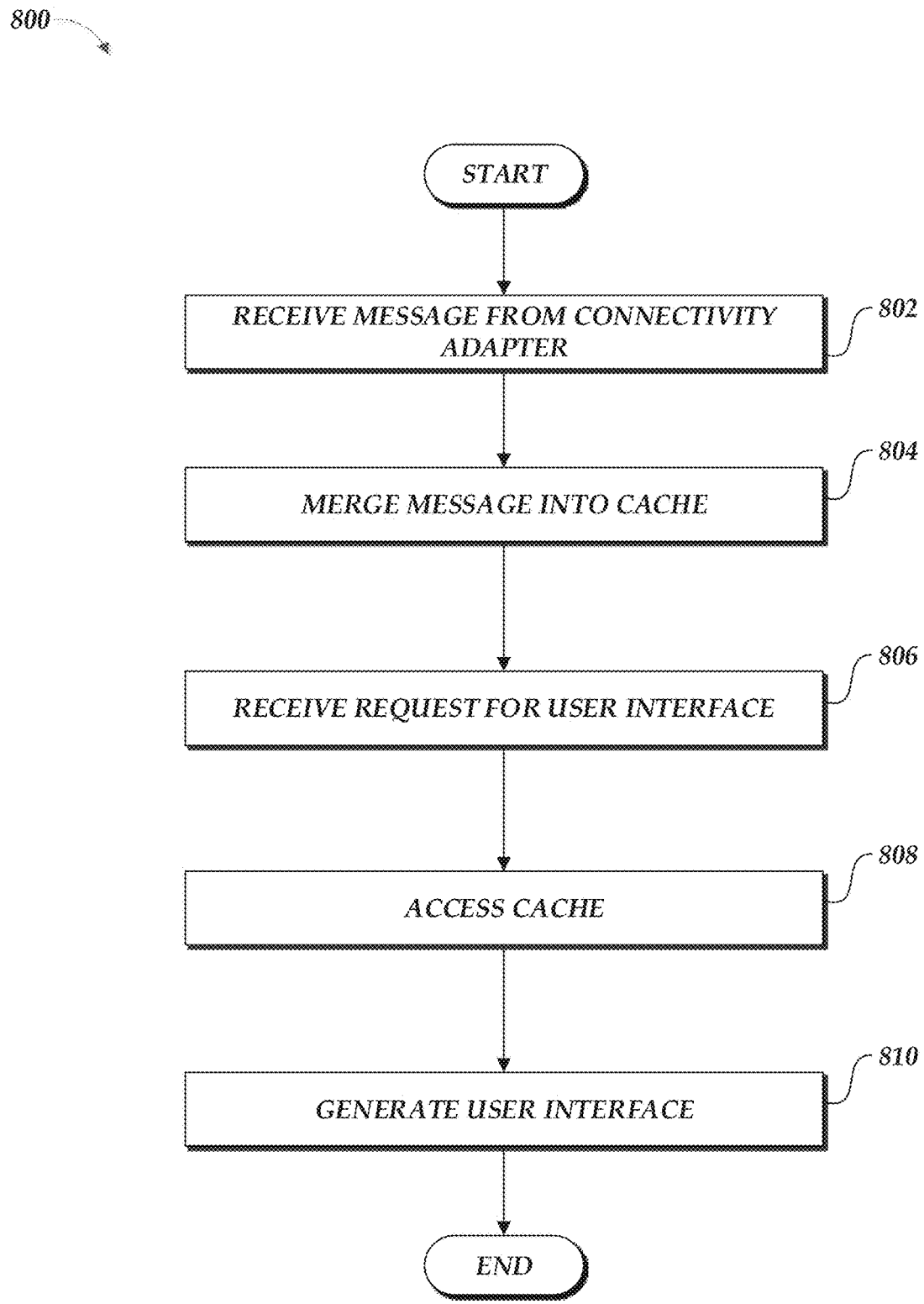
FIG. 8 is a flow diagram illustrating an example method for merging messages into a cache in accordance with aspects of the present disclosure.

With reference now to FIG. 8, an example message merging and caching method 800 will be described. The example method 800 may be carried out, for example, by the DFM 408 of FIG. 5 (or one or more components thereof). The method 800 illustrates an example algorithm that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then executed by the CPU or microcontroller. For example, when the method 800 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. In some embodiments, the method 800 or portions thereof may be implemented on multiple processors, serially or in parallel. For convenience, the steps of the example method 800 are described as being performed by the DFM 408.

At block 802, the DFM 408 receives a message from the connectivity adapter 206. As discussed above, the message may reflect the current state of the infusion pump 204 connected to the connectivity adapter 206 and may be in the standardized dataset format.

At block 804, the DFM 408 merges the message into the cache 408A. In some cases, the DFM 408 determines whether the message is relevant to any potential UI generation requests (e.g., may be used to generate a UI provided to the clinical environment 102). Based on determining that the message is relevant to a potential UI generation request, the DFM 408 may merge the message into the cache 408A. Alternatively, based on determining that the message is not relevant to a potential UI generation request, the DFM 408 may refrain from merging the message into the cache 408A and merge the message into a database (e.g., database 414). In other embodiments, the DFM 408 may merge the message into the cache 408A, and remove the information included in the message from the cache 408A to the database 414 based on a determination that the message is not relevant to a potential UI generation request (e.g., after a specific time window).

At block 806, the DFM 408 receives a request to generate a user interface (e.g., from the clinical environment 102). The user interface data to be generated may be based on information previously provided by the connectivity adapter 206 (e.g., pump status, infusion status, power status, etc.).

At block 808, the DFM 408 accesses the cache 408A for information to be used for generating the user interface. For example, the information may include the current state of a single infusion pump, multiple infusion pumps in communication with a single connectivity adapter at a single facility, multiple infusion pumps in communication with multiple connectivity adapters at a single facility, multiple infusion pumps at multiple facilities, or any combination thereof.

At block 810, the DFM 408 provides the information accessed from the cache 408A to other services such as the report manager 404 or the device manager 406. Such services may generate the user interface and transmit the generated user interface to the clinical environment 102 (e.g., for presentation via the cloud user interface 208). In some cases, the requested user interface data are pre-generated by such services and stored in the cache 408A. In such cases, the such services can simply access and transmit the user interface data stored in the cache 408A to the clinical environment 102 or update the user interface data stored in the cache 408A before transmitting them to the clinical environment 102.

In the method 800, one or more of the blocks shown in FIG. 8 may be removed (e.g., not performed) and/or the order in which the method 800 is performed may be switched. In some embodiments, additional blocks may be added to the method 800. The embodiments of the present disclosure are not limited to or by the example shown in FIG. 8, and other variations may be implemented without departing from the spirit of this disclosure.

Pump Message Conversion Method

Figure 9:
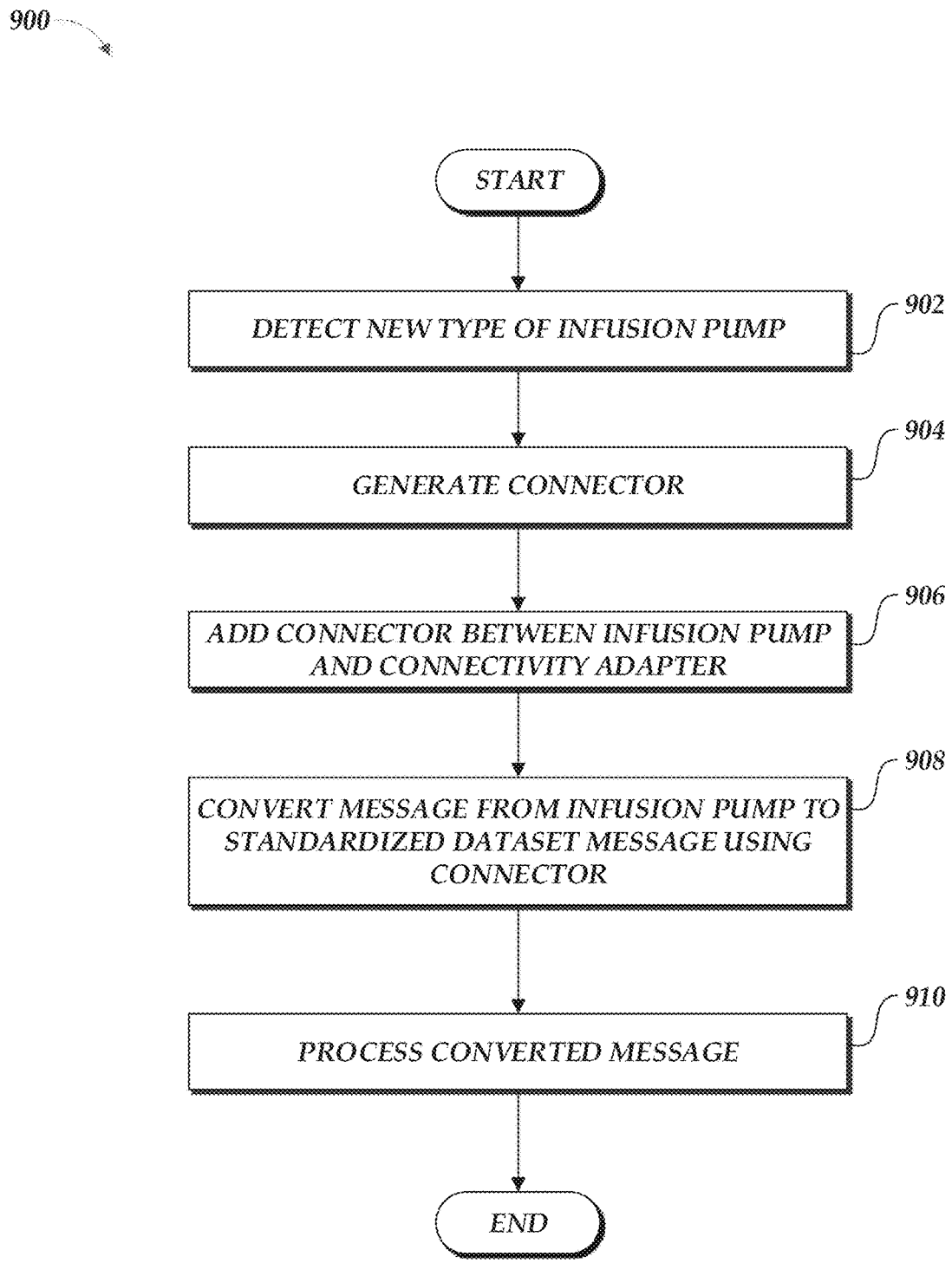
FIG. 9 is a flow diagram illustrating an example method for converting a pump message to a standardized dataset message in accordance with aspects of the present disclosure.

With reference now to FIG. 9, an example pump message conversion method 900 connectivity adapter 206 of FIG. 3 (or one or more components thereof). The method 900 illustrates an example algorithm that may be programmed, using any suitable programming environment or language, to create machine code capable of execution by a CPU or microcontroller of the connectivity adapter 206. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of connectivity adapter 206 that is coupled to the CPU or microcontroller and then executed by the CPU or microcontroller. For example, when the method 900 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. In some embodiments, the method 900 or portions thereof may be implemented on multiple processors, serially or in parallel. For convenience, the steps of the example method 900 are described as being performed by the transformation worker 206A.

At block 902, the transformation worker 206A detects a new type of infusion pump that uses a new pump protocol. For example, the transformation worker 206A may check the device ID or protocol ID associated with the infusion pump and determine that the device ID or protocol ID does not match a predetermined list of device IDs or protocol IDs.

At block 904, the transformation worker 206A generates a connector (e.g., a software module or a set of computer executable instructions) for converting messages in the new pump protocol to the standardized dataset messages. For example, the transformation worker 206A may download a new configuration file that can be used to implement the connector from the cloud environment 106. Alternatively, the transformation worker 206A may access the parameters included in a message in the new pump protocol and compare the parameters to the parameters in a standardized dataset message to generate a mapping between the two sets of parameters.

At block 906, the transformation worker 206A adds the connector between one or more infusion pumps using the new pump protocol. For example, the transformation worker 206A may add the protocol ID to the list of mappings that the transformation worker 206A is configured to perform. The transformation worker 206A may add the protocol ID to the list of mappings that the transformation worker 206A checks for upon receiving a pump message.

At block 908, the transformation worker 206A converts a message from the infusion pump using the new pump protocol to a standardized dataset message using the connector.

At block 910, the transformation worker 206A processes the converted message. For example, the transformation worker 206A may send the message to the device status manager 206B to be merged into the cache 206C and/or added to the outbound queue 206D.

In the method 900, one or more of the blocks shown in FIG. 9 may be removed (e.g., not performed) and/or the order in which the method 900 is performed may be switched. In some embodiments, additional blocks may be added to the method 900. The embodiments of the present disclosure are not limited to or by the example shown in FIG. 9, and other variations may be implemented without departing from the spirit of this disclosure.

Cloud Authentication via Proxy

Figure 10:
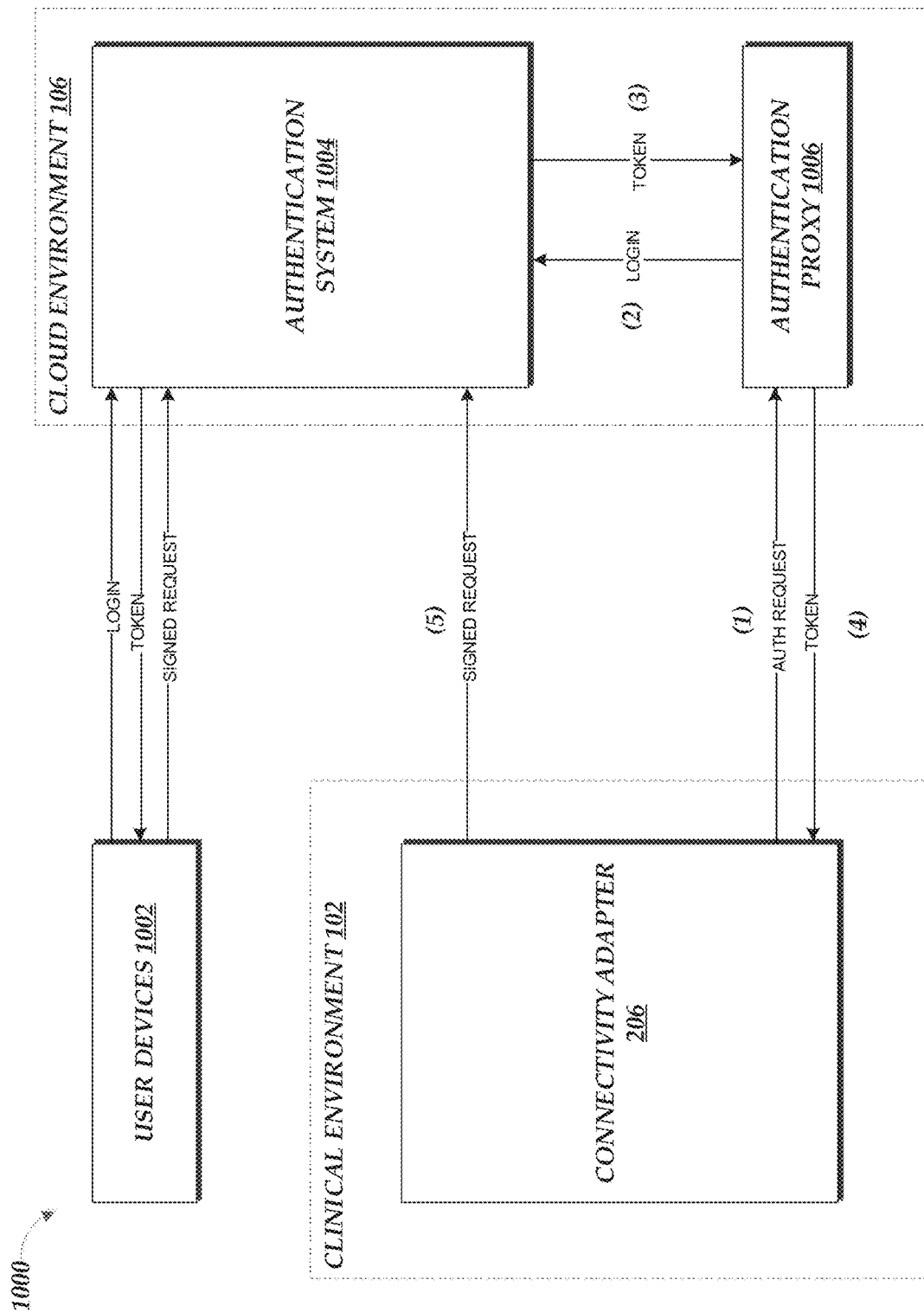
FIG. 10 is a schematic diagram illustrating an example method for authenticating a connectivity adapter using an authentication proxy in accordance with aspects of this disclosure.

FIG. 10 illustrates a computing environment 1000 including user device 1002, the clinical environment 102 including the connectivity adapter 206, and the cloud environment 106 including authentication system 1004 and authentication proxy 1006. As shown in FIG. 10, the authentication system 1004 may be configured to authenticate users based on login requests from the user devices 1002, and provide cloud services to user devices 1002 that are successfully authenticated. In such cases, the user device 1002 may own user accounts created by the authentication system 1004 and provide the login credentials for the user accounts each time accessing the cloud services provided by the cloud environment 106.

In some cases, the connectivity adapter 206 may be a network appliance and may lack the capability of managing and maintaining its own user account. In such cases, the connectivity adapter 206 may send an authentication request to the authentication proxy 1006 (e.g., via a connection such as a secured and authenticated WebSocket connection or another other TCP connection), and the authentication proxy 1006 may provide login credentials to the authentication system 1004 on behalf of the connectivity adapter 206 and receive a security token that can be used by the connectivity adapter 206 to generate a signed request. The connectivity adapter 206 may send the signed request to the authentication system 1004 (e.g., using HTTP), just as the authenticated user devices 1002 do in FIG. 10. In some cases, the connection between the connectivity adapter 206 and the authentication proxy 1006 utilize a different communications protocol (e.g., WebSocket) than the connection between the connectivity adapter 206 and the authentication system 1004 (e.g., HTTP). By using the authentication proxy 1006, the connectivity adapter can utilize the cloud services provided by the cloud environment 106 without having to manage user accounts or login credentials. The authentication proxy 1006 may maintain one or more user accounts per clinical environment account.

Connectivity Adapter Authentication Method

Figure 11:
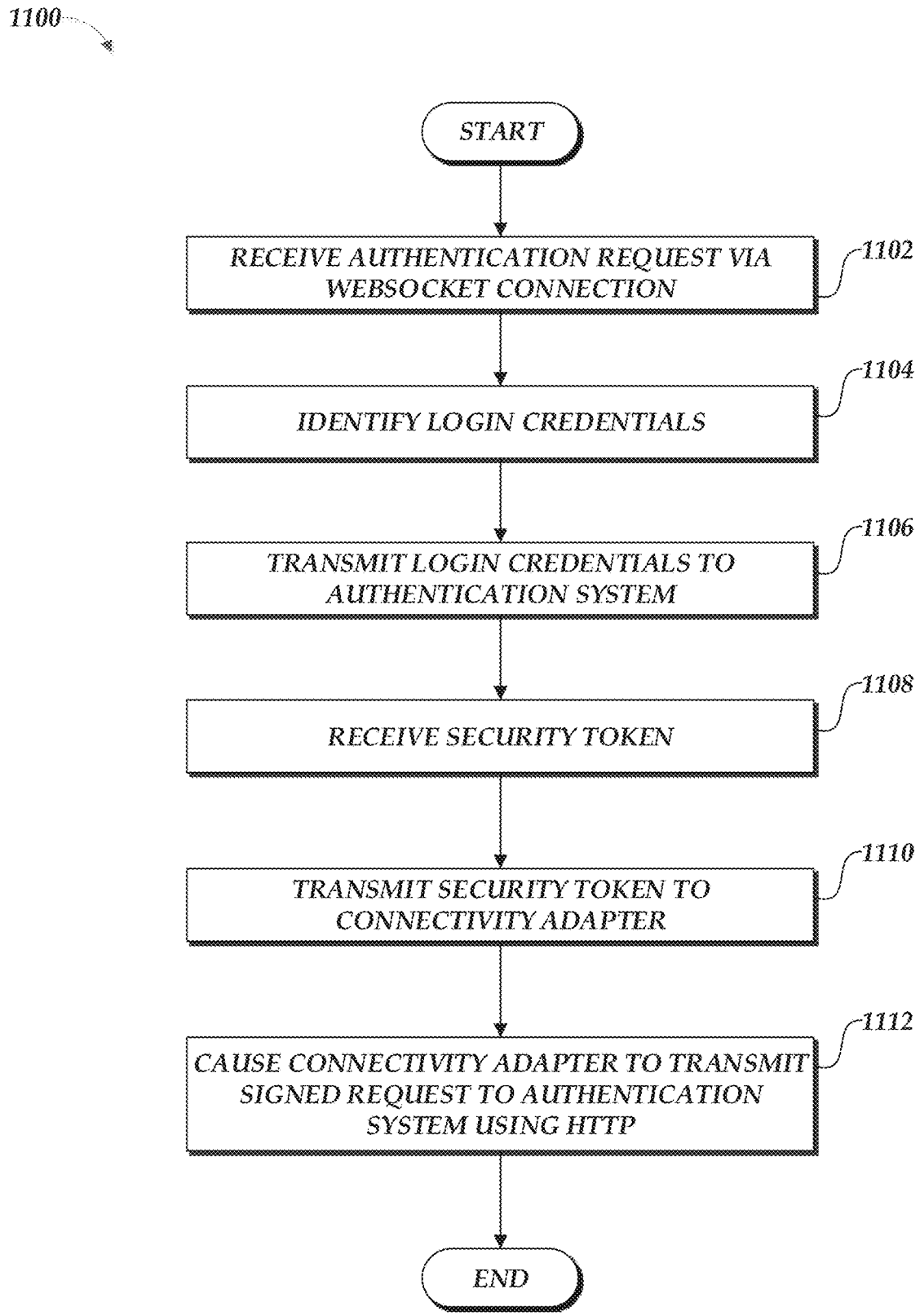
FIG. 11 is a flow diagram illustrating an example method for authenticating a connectivity adapter using an authentication proxy in accordance with aspects of this disclosure.

With reference now to FIG. 11, an example connectivity adapter authentication method 1100 will be described. The example method 1100 may be carried out, for example, by the authentication proxy 1006 of FIG. 10. The method 1100 illustrates an example algorithm that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then executed by the CPU or microcontroller. For example, when the method 1100 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. In some embodiments, the method 1100 or portions thereof may be implemented on multiple processors, serially or in parallel. For convenience, the steps of the example method 1100 are described as being performed by the authentication proxy 1006.

At block 1102, the authentication proxy 1006 receives an authentication request from the connectivity adapter 206 via a secured and authenticated WebSocket connection. For example, the WebSocket connection may be the connection via which the connectivity adapter 206 transmits messages to the cloud environment 106.

At block 1104, the authentication proxy 1006 identifies the login credentials of a user account to be used for authenticating the connectivity adapter 206. For example, the authentication proxy 1006 may identify the user account based on one or more identifiers associated with the clinical environment 102. In some embodiments, the clinical environment 102 is associated with a one or more identifiers and has multiple regions, healthcare systems, and facilities therein.

At block 1106, the authentication proxy 1006 transmits the login credentials to the authentication system 1004, and at block 1108, the authentication proxy 1006 receives a security token from the authentication system 1004.

At block 1110, the authentication proxy 1006 transmits the security token to the connectivity adapter 206, and at block 1112, the authentication proxy 1006 causes the connectivity adapter 206 to transmit a signed request to the authentication system using HTTP.

In the method 1100, one or more of the blocks shown in FIG. 11 may be removed (e.g., not performed) and/or the order in which the method 1100 is performed may be switched. In some embodiments, additional blocks may be added to the method 1100. The embodiments of the present disclosure are not limited to or by the example shown in FIG. 11, and other variations may be implemented without departing from the spirit of this disclosure.

Data Segmentation

Figure 12:
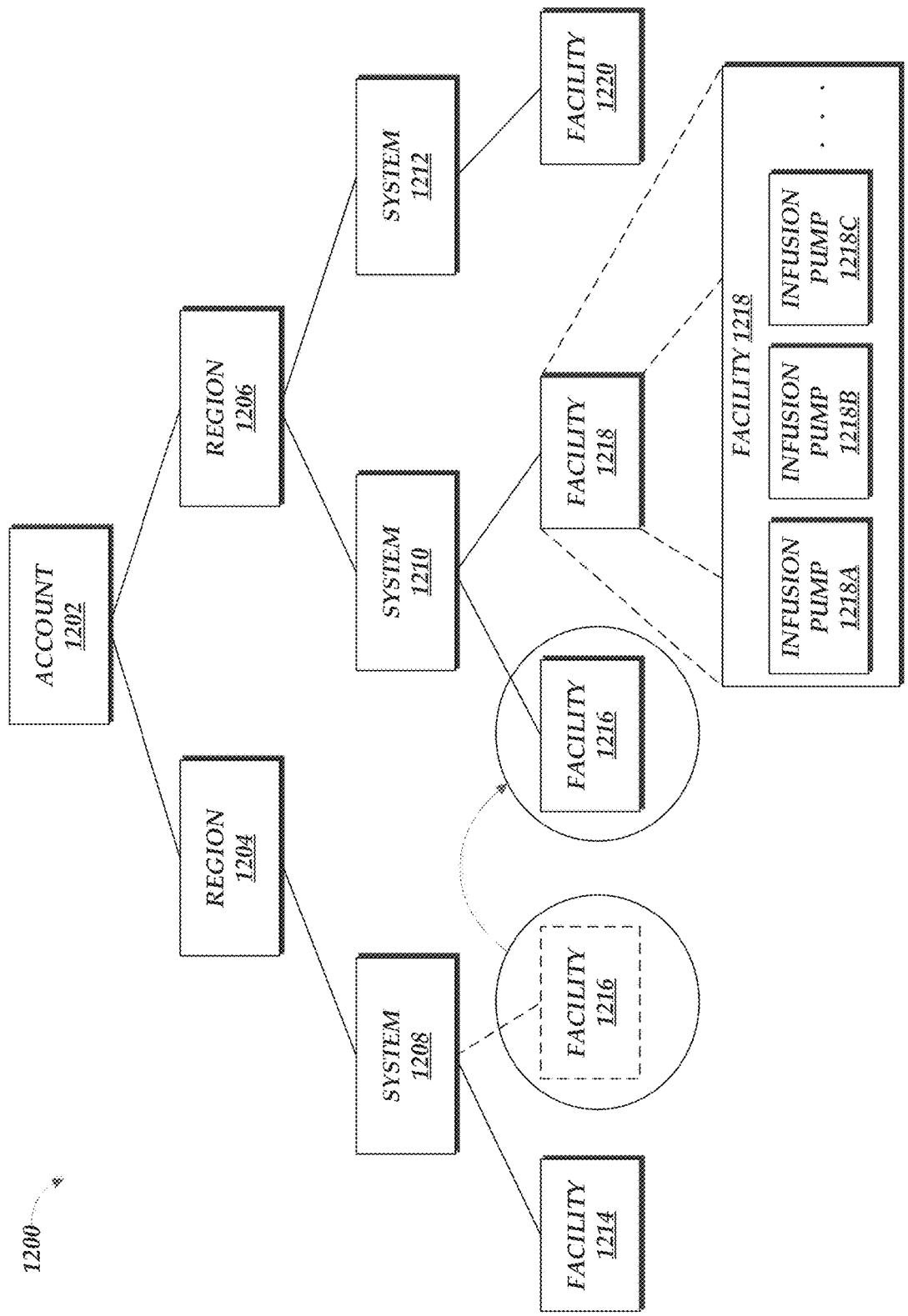
FIG. 12 is a block diagram illustrating a segmented data structure in accordance with aspects of the present disclosure.

FIG. 12 shows a block diagram illustrating a segmented data structure 1200 including an account data node 1202, which includes region data nodes 1204 and 1206. The region data node 1204 includes system data node 1208, and the region data node 1206 includes system data nodes 1210 and 1212. The system data node 1208 includes facility data node 1214. As shown in FIG. 12, facility data node that used to belong to the system data node 1208 has been moved to the system data node 1210, which further includes facility data node 1218. The system data node 1212 includes facility data node 1220. As shown in FIG. 12, the facility data node includes infusion pumps 1218A, 1218B, 1218C, etc. The account data node 1202 corresponds to an account generated for each unique entity that may own, oversee, and/or manage one or more healthcare facilities (e.g., hospital facilities) in one or more healthcare systems (e.g., a network of hospitals) in one or more regions (e.g., geographical divisions including multiple networks of hospitals). For example, the clinical environment 102 may correspond to any of a facility, system, region, or account.

In some embodiments, the data generated by the infusion pumps 204 and/or the connectivity adapters 206 at the individual facilities may be tagged with the facility ID and the account ID, since those two identifiers may be permanent. For example, the connectivity adapter 206 may receive a message from the infusion pump 204, convert the message into a standardized dataset message, and inject one or more tags into the standardized dataset message by adding or setting one or more corresponding key-value pairs (e.g., facilityID=F0293, accountID=A29847, etc.) in the standardized dataset message. On the other hand, as the facilities are restructured and moved around within the enterprise structure, the data corresponding to the facilities may be assigned a different system ID or region ID. For example, in the example of FIG. 12, the facility data node 1216 has been moved from the system data node 1208 to system data node 1210 (e.g., representative of a change in the boundary between two regions), the data generated at the facility corresponding to the facility data node 1216, while still belonging to the facility data node 1216 and account data node 1202, no longer belongs to the system data node 1208 and region data node 1204, and instead belongs to the system data node 1210 and region data node 1206. Thus, by tagging the messages prior to transmitting them to the cloud environment 106 with immutable IDs (e.g., facility ID and account ID) and not IDs that may or may not change in the future, the connectivity adapter 206 facilitates security control, access, filtering, and reporting of such data. Further, as a result, the infusion pumps 204 need not be aware or keep track of the facility to which they are connected, since any messages or other data generated by the infusion pumps 204 will be appropriately tagged by the connectivity adapter 206 to which they are connected. For example, if an infusion pump is moved from one facility to another, the infusion pump can simply start sending messages to the connectivity adapter 206 at the new facility without worrying about the change in facility, since any new data generated by the infusion pump at the new facility will be tagged with the new facility ID by the new connectivity adapter 206. Further, by allowing the facilities to be moved across systems and regions, the segmented data structure 1200 allows facilities having one characteristic to be decoupled from other facilities having another characteristic (e.g., EHR vendor A vs. EHR vendor B, pump type X vs. pump type Y, etc.).

In some embodiments, data generated by the infusion pumps and/or connectivity adapters may include a facility ID and an account ID as immutable (permanent) IDs, and may include one or more mutable IDs such as a region ID and a system ID. The IDs associated with the data generated in a given facility may reflect the structural associations at the time of generation (old structure). When the facility is later restructured (new structure), the new structure is used in connection with the data (e.g., for reporting the data) and the prior mutable IDs may be ignored or updated as needed. Thus, data records are tagged based on the structure (e.g., account, region, system, facility) at the time that the data records are created. When the structure is subsequently modified, the system can (i) continue to use the data records as tagged at the time of creation despite the changes, (ii) update the mutable IDs to reflect the modified structure, and use the data records with the immutable IDs and updated mutable IDs, (iii) use the data records with only the immutable IDs (e.g., ignoring the mutable IDs), or (iv) use the data records with the immutable IDs and any mutable IDs that still reflect the modified structure.

Segmented Data Restructuring Method

Figure 13:
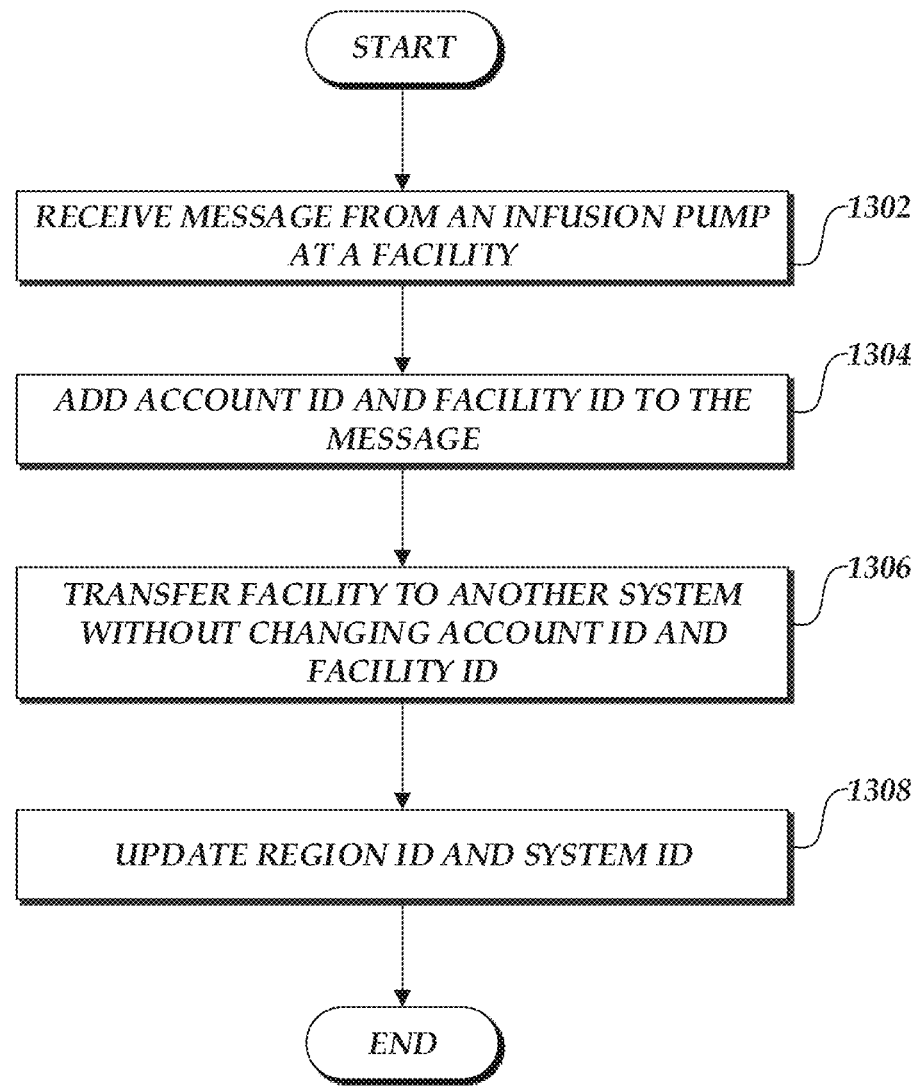
FIG. 13 is a flow diagram illustrating an example method for moving data nodes in a segmented data structure in accordance with aspects of this disclosure.

With reference now to FIG. 13, an example segmented data restructuring method 1300 will be described. The example method 1300 may be carried out, for example, by the connectivity adapter 206 of FIG. 3 (or one or more components thereof) or the cloud environment 106 of FIG. 5 (or one or more components thereof). The method 1300 illustrates an example algorithm that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then executed by the CPU or microcontroller. For example, when the method 1300 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. In some embodiments, the method 1300 or portions thereof may be implemented on multiple processors, serially or in parallel. For convenience, the steps of the example method 1300 are described as being performed by the connectivity adapter 206 and/or the cloud environment 106.

At block 1302, the connectivity adapter 206 receives a message from an infusion pump 204 at a facility (e.g., hospital).

At block 1304, the connectivity adapter 206 adds an account ID and a facility ID to the message received from the infusion pump 204. In some cases, the message from the infusion pump 204 may be converted to a standardized dataset message, and the account ID and facility ID may be added to the standardized dataset message. In some embodiments, the connectivity adapter 206 determines one or more IDs described herein (e.g., account ID, facility ID, region ID, system ID, etc.) associated with the infusion pump 204 by checking one or more indicators in a priority order. For example, the connectivity adapter 206 may determine a given indicator associated with the infusion pump 204 and access a database of facility IDs (or other IDs) to determine whether any of the facility IDs are associated with the determined indicator associated with the infusion pump 204. The indicator may be one or more of (i) the network port via which the infusion pump 204 is connected to the connectivity adapter 206 (e.g., pumps associated with Facility A may connect via Port 9292, pumps associated with Facility B may connect via Port 9293, etc.), (ii) location data associated with the infusion pump 204, (iii) the Internet Protocol (IP) address associated with the infusion pump 204, (iv) the name associated with the infusion pump 204, (v) the Media Access Control (MAC) address associated with the infusion pump 204, (vi) the Wi-Fi access point associated with the infusion pump 204, and (vii) the serial number associated with the infusion pump 204. If the connectivity adapter 206 determines, after checking one or more of the indicators, that the facility ID (or another ID) cannot be found in the database, the connectivity adapter 206 may add a default facility ID to the message received from the infusion pump 204 at block 1304, indicating that the pump message originated from an infusion pump not associated with a known facility.

In some embodiments, one or more of the indicators described herein are checked in a specific priority order. For example, the connectivity adapter 206 may first try to determine the facility ID (or another ID) based on the MAC address of the infusion pump 204. If the connectivity adapter 206 does not find a facility ID matching the MAC address, the connectivity adapter 206 may then try to determine the facility ID based on the serial number of the infusion pump 204. If the connectivity adapter 206 does not find a facility ID matching the serial number, the connectivity adapter 206 may then try to determine the facility ID based on the location data associated with the infusion pump 204. If the connectivity adapter 206 does not find a facility ID matching the location data, the connectivity adapter 206 may add a default facility ID to the message received from the infusion pump 204 at block 1304, indicating that the pump message originated from an infusion pump not associated with a known facility. Although the priority order of MAC address, serial number, and location data is used as an example, the techniques described herein can be applied to any other combination of indicators may be checked in any other priority order.

At block 1306, the cloud environment 106 transfers the facility at which the infusion pump 204 is located to another system (e.g., a healthcare system or a network of facilities) without changing the account ID and the facility ID of the message. For example, the facility may be using the EMR system from vendor A, and all facilities using the EMR system from vendor A within the existing healthcare system may have been separated out to a new healthcare system.

At block 1308, the cloud environment 106 updates the region ID and the system ID associated with the facility in which the infusion pump 204 is located. By updating the region ID and system ID of the facility, any new data generated in the facility may be accessible using the new region ID and system ID. Further, even after moving the facility 1216 from the system 1208 to the system 1210, the pump messages generated by the infusion pumps at the facility 1216 may continue to be stamped, tagged, or otherwise associated with the same account ID and the facility ID as those used prior to the move. In some cases, when an infusion pump is physically moved to a new facility, the connectivity adapter 206 at the new facility may stamp, tag, or otherwise associate the pump messages generated by the infusion pump with a new facility ID corresponding to the new facility.

In the method 1300, one or more of the blocks shown in FIG. 13 may be removed (e.g., not performed) and/or the order in which the method 1300 is performed may be switched. In some embodiments, additional blocks may be added to the method 1300. The embodiments of the present disclosure are not limited to or by the example shown in FIG. 13, and other variations may be implemented without departing from the spirit of this disclosure.

Example Clauses

Embodiments of the present disclosure can be defined by the following non-limiting clauses:

Clause 1. A system configured to facilitate messaging during a network outage, the system comprising: a plurality of infusion pumps configured to deliver medication to patients, each infusion pump of the plurality of infusion pumps comprising a memory configured to store operational software and a processor configured to generate pump messages; a connectivity adapter comprising computer hardware and in communication with the plurality of infusion pumps over a first network; and a server comprising computer hardware and in communication with the connectivity adapter over a second network different from the first network, wherein the connectivity adapter is configured to: receive a first pump message from a first infusion pump of the plurality of infusion pumps, the first pump message including information that is new to the connectivity adapter; generate a first standardized dataset message based on the information in the first pump message; store the first standardized dataset message in an outbound queue for transmission to the server; subsequent to storing the first standardized dataset message in the outbound queue, receive a second pump message from the first infusion pump, the second pump message including additional information that is new to the connectivity adapter; generate a second standardized dataset message based on the additional information in the second pump message; store the second standardized dataset message in the outbound queue for transmission to the server; remove the first standardized dataset message from the outbound queue without transmitting the first standardized dataset message to the server; and transmit the second standardized dataset message in the outbound queue to the server.

Clause 2. The system of Clause 1, wherein the first pump message includes a first message identifier (ID), and the second pump message includes a second message ID that immediately follows the first message ID in value.

Clause 3. The system of Clause 1, wherein the first standardized dataset message includes a first message identifier (ID), and the second standardized dataset message includes a second message ID that immediately follows the first message ID in value.

Clause 4. The system of Clause 1, wherein the first pump message includes a first parameter indicative of a status of the first infusion pump, and the first standardized dataset message includes (i) the first parameter and (ii) a second parameter that is not in the first pump message and indicative of another status of the first infusion pump.

Clause 5. The system of Clause 4, wherein the second parameter is associated with one of a null value or a default value.

Clause 6. The system of Clause 1, wherein the connectivity adapter is further configured to store the information in the first pump message in a cache.

Clause 7. The system of Clause 6, wherein the connectivity adapter is further configured to receive a third pump message from the first infusion pump, and based on determining that the third pump message does not include information new to the connectivity adapter, refrain from storing the information in the third pump message in the cache.

Clause 8. The system of Clause 1, wherein the connectivity adapter is further configured to update a parameter stored in a cache based on the information in the first pump message.

Clause 9. The system of Clause 1, wherein the connectivity adapter is further configured to, subsequent to removing the first standardized dataset message from the outbound queue without transmitting the first standardized dataset message to the server, receive a request for the first pump message from the server.

Clause 10. The system of Clause 9, wherein the connectivity adapter is further configured to, in response to the request for the first pump message, transmit a request for the first pump message to the first infusion pump.

Clause 11. A method of facilitating messaging during a network outage, the method comprising: receiving a first pump message from a first infusion pump over a first network; generating a first standardized dataset message based on the information in the first pump message; storing the first standardized dataset message in an outbound queue for transmission to a server over a second network different from the first network; subsequent to storing the first standardized dataset message in the outbound queue, receiving a second pump message from the first infusion pump over the first network; generating a second standardized dataset message based on the additional information in the second pump message; storing the second standardized dataset message in the outbound queue for transmission to the server; removing the first standardized dataset message from the outbound queue without transmitting the first standardized dataset message to the server; and transmitting the second standardized dataset message in the outbound queue to the server over the second network.

Clause 12. The method of Clause 11, wherein the first pump message includes a first message identifier (ID), and the second pump message includes a second message ID that immediately follows the first message ID in value.

Clause 13. The method of Clause 11, wherein the first standardized dataset message includes a first message identifier (ID), and the second standardized dataset message includes a second message ID that immediately follows the first message ID in value.

Clause 14. The method of Clause 11, wherein the first pump message includes a first parameter indicative of a status of the first infusion pump, and the first standardized dataset message includes (i) the first parameter and (ii) a second parameter that is not in the first pump message and indicative of another status of the first infusion pump.

Clause 15. The method of Clause 14, wherein the second parameter is associated with one of a null value or a default value.

Clause 16. The method of Clause 11, further comprising storing the information in the first pump message in a cache.

Clause 17. The method of Clause 16, further comprising receiving a third pump message from the first infusion pump, and based on determining that the third pump message does not include information new to the connectivity adapter, refraining from storing the information in the third pump message in the cache.

Clause 18. The method of Clause 11, further comprising updating a parameter stored in a cache based on the information in the first pump message.

Clause 19. The method of Clause 11, further comprising, subsequent to removing the first standardized dataset message from the outbound queue without transmitting the first standardized dataset message to the server, receiving a request for the first pump message from the server.

Clause 20. The method of Clause 19, further comprising, in response to the request for the first pump message, transmitting a request for the first pump message to the first infusion pump.

Clause 21. A system configured to facilitate messaging during a network outage, the system comprising: a plurality of infusion pumps configured to deliver medication to patients, each infusion pump of the plurality of infusion pumps comprising a memory configured to store operational software and a processor configured to generate pump messages; a connectivity adapter comprising computer hardware and in communication with the plurality of infusion pumps over a first network; and a server comprising computer hardware and in communication with the connectivity adapter over a second network different from the first network, wherein the connectivity adapter is configured to: receive a first pump message from a first infusion pump of the plurality of infusion pumps, the first pump message including information that is new to the connectivity adapter; generate a first standardized dataset message based on the information in the first pump message; store the first standardized dataset message in an outbound queue for transmission to the server; subsequent to storing the first standardized dataset message in the outbound queue, receive a second pump message from the first infusion pump, the second pump message including additional information that is new to the connectivity adapter; generate a second standardized dataset message based on the additional information in the second pump message; store the second standardized dataset message in the outbound queue for transmission to the server; determine whether a removal condition for removing the first standardized dataset message from the outbound queue without transmitting the first standardized dataset message to the server is satisfied; and subsequent to determining whether the removal condition is satisfied, removing the first standardized dataset message from the outbound queue.

Clause 22. The system of Clause 21, wherein the connectivity adapter is further configured to, subsequent to determining that the removal condition is satisfied, remove the first standardized dataset message from the outbound queue without transmitting the first standardized dataset message to the server.

Clause 23. The system of Clause 21, wherein the connectivity adapter is further configured to, subsequent to determining that the removal condition is not satisfied, remove the first standardized dataset message from the outbound queue and transmit the first standardized dataset message to the server.

Clause 24. The system of Clause 22 or 23, wherein determining whether the removal condition is satisfied comprises determining whether the first standardized dataset message has been in the outbound queue for a time period greater than a threshold time period.

Clause 25. The system of Clause 22 or 23, wherein determining whether the removal condition is satisfied comprises determining whether the outbound queue includes a number of messages that is greater than a threshold number of messages.

Clause 26. The system of Clause 22 or 23, wherein the first pump message includes a first message identifier (ID), and the second pump message includes a second message ID that immediately follows the first message ID in value.

Clause 27. The system of Clause 22 or 23, wherein the first standardized dataset message includes a first message identifier (ID), and the second standardized dataset message includes a second message ID that immediately follows the first message ID in value.

Clause 28. The system of Clause 22 or 23, wherein the first pump message includes a first parameter indicative of a status of the first infusion pump, and the first standardized dataset message includes (i) the first parameter and (ii) a second parameter that is not in the first pump message and indicative of another status of the first infusion pump.

Clause 29. The system of Clause 28, wherein the second parameter is associated with one of a null value or a default value.

Clause 30. The system of Clause 22 or 23, wherein the connectivity adapter is further configured to store the information in the first pump message in a cache.

Clause 31. The system of Clause 30, wherein the connectivity adapter is further configured to receive a third pump message from the first infusion pump, and based on determining that the third pump message does not include information new to the connectivity adapter, refrain from storing the information in the third pump message in the cache.

Clause 32. The system of Clause 22 or 23, wherein the connectivity adapter is further configured to update a parameter stored in a cache based on the information in the first pump message.

Clause 33. The system of Clause 22, wherein the connectivity adapter is further configured to, subsequent to removing the first standardized dataset message from the outbound queue without transmitting the first standardized dataset message to the server, receive a request for the first pump message from the server.

Clause 34. The system of Clause 33, wherein the connectivity adapter is further configured to, in response to the request for the first pump message, transmit a request for the first pump message to the first infusion pump.

Clause 35. A method for providing messaging in a clinical environment, the method comprising: storing a plurality of messages in a message queue, wherein the plurality of messages contain information about one or more infusion pumps residing in the clinical environment, the plurality of messages stored in the message queue including at least a first message and a second message; transmitting at least some of the plurality of messages to a remote server configured to receive messages generated in the clinical environment; subsequent to the transmission, detecting a network outage, wherein the network outage prevents transmission of messages to the remote server; determining that the first message in the message queue satisfies a condition for being removed from the message queue without being successfully transmitted to the remote server; removing the first message from the message queue such that the first message is removed from the message queue prior to being received by the remote server; determining that the network outage has been resolved; and transmitting the second message to the remote server such that the second message is received by the remote server and the first message is not received by the remote server.

Clause 36. The method of Clause 35, further comprising detecting the network outage based at least on not having received an acknowledgement from the remote server during a specific time window.

Clause 37. The method of Clause 35, further comprising detecting the network outage based at least on receiving a message from the remote server that a connection to the remote server is terminated.

Clause 38. The method of Clause 35, further comprising determining that the first message satisfies the condition based at least on the first message being associated with an infusion pump event that is older than a threshold amount of time.

Clause 39. The method of Clause 35, further comprising determining that the first message satisfies the condition based at least on the first message being the oldest message in the message queue.

Clause 40. The method of Clause 35, further comprising determining that the first message satisfies the condition based at least on the message queue being full.

Clause 41. The method of Clause 35, further comprising attempting, prior to determining that the first message satisfies the condition, to transmit the first message to the remote server, and determining that the first message was not received by the remote server.

Clause 42. An apparatus configured to provide messaging in a clinical environment, the apparatus comprising: one or more processors; and one or more memories in communication with the one or more processors and storing computer-executable instructions that, when executed by the one or more processors, configure the one or more processors to: cause a plurality of messages to be stored in a message queue, wherein the plurality of messages contain information about one or more infusion pumps residing in the clinical environment, the plurality of messages stored in the message queue including at least a first message and a second message; cause at least some of the plurality of messages to be transmitted to a remote server configured to receive messages generated in the clinical environment; subsequent to the transmission, determine that the first message in the message queue satisfies a condition for being removed from the message queue; cause the first message to be removed from the message queue such that the first message is removed from the message queue prior to being received by the remote server; and cause the second message to be transmitted to the remote server such that the second message is received by the remote server and the first message is not received by the remote server.

Clause 43. The apparatus of Clause 42, wherein the computer-executable instructions, when executed by the one or more processors, further configure the one or more processors to detect a network outage that prevents transmission of messages to the remote server.

Clause 44. The apparatus of Clause 43, wherein the computer-executable instructions, when executed by the one or more processors, further configure the one or more processors to detect the network outage based at least on not having received an acknowledgement from the remote server during a specific time window.

Clause 45. The apparatus of Clause 43, wherein the computer-executable instructions, when executed by the one or more processors, further configure the one or more processors to detect the network outage based at least on receiving a message from the remote server that a connection to the remote server is terminated.

Clause 46. The apparatus of Clause 42, wherein the computer-executable instructions, when executed by the one or more processors, further configure the one or more processors to determine that the first message satisfies the condition based at least on the first message being associated with an infusion pump event that is older than a threshold amount of time.

Clause 47. The apparatus of Clause 42, wherein the computer-executable instructions, when executed by the one or more processors, further configure the one or more processors to determine that the first message satisfies the condition based at least on the first message being the oldest message in the message queue.

Clause 48. The apparatus of Clause 42, wherein the computer-executable instructions, when executed by the one or more processors, further configure the one or more processors to determine that the first message satisfies the condition based at least on the message queue being full.

Clause 49. The apparatus of Clause 42, wherein the computer-executable instructions, when executed by the one or more processors, further configure the one or more processors to attempt, prior to determining that the first message satisfies the condition, to transmit the first message to the remote server, and determine that the first message was not received by the remote server.

Clause 50. Non-transitory physical computer storage storing computer-executable instructions that, when executed by one or more computing devices, configure the one or more computing devices to: cause a plurality of messages to be stored in a message queue, wherein the plurality of messages contain information about one or more infusion pumps residing in the clinical environment, the plurality of messages stored in the message queue including at least a first message and a second message; cause at least some of the plurality of messages to be transmitted to a remote server configured to receive messages generated in the clinical environment; subsequent to the transmission, determine that the first message in the message queue satisfies a condition for being removed from the message queue; cause the first message to be removed from the message queue such that the first message is removed from the message queue prior to being received by the remote server; and cause the second message to be transmitted to the remote server such that the second message is received by the remote server and the first message is not received by the remote server.

Clause 51. The non-transitory physical computer storage of Clause 50, wherein the computer-executable instructions, when executed by the one or more computing devices, further configure the one or more computing devices to detect a network outage that prevents transmission of messages to the remote server.

Clause 52. The non-transitory physical computer storage of Clause 50, wherein the computer-executable instructions, when executed by the one or more computing devices, further configure the one or more computing devices to determine that the first message satisfies the condition based at least on the first message being associated with an infusion pump event that is older than a threshold amount of time.

Clause 53. The non-transitory physical computer storage of Clause 50, wherein the computer-executable instructions, when executed by the one or more computing devices, further configure the one or more computing devices to determine that the first message satisfies the condition based at least on the first message being the oldest message in the message queue.

Clause 54. The non-transitory physical computer storage of Clause 50, wherein the computer-executable instructions, when executed by the one or more computing devices, further configure the one or more computing devices to attempt, prior to determining that the first message satisfies the condition, to transmit the first message to the remote server, and determine that the first message was not received by the remote server.

Clause 55. A method for providing messaging in a clinical environment, the method comprising: storing a plurality of messages in a message queue, wherein the plurality of messages contain information about one or more infusion pumps residing in the clinical environment, the plurality of messages stored in the message queue including at least a first message; transmitting at least some of the plurality of messages to a remote server configured to receive messages generated in the clinical environment; subsequent to the transmission, detecting a temporary interruption in a network connection to the remote server, wherein the temporary interruption prevents transmission of messages to the remote server; determining that the first message in the message queue does not satisfy a condition for being removed from the message queue without being successfully transmitted to the remote server; determining that the temporary interruption has been resolved; and transmitting the first message to the remote server such that the first message is received by the remote server.

Clause 56. The method of Clause 55, further comprising detecting the temporary interruption based at least on not having received an acknowledgement from the remote server during a specific time window.

Clause 57. The method of Clause 55, further comprising detecting the temporary interruption based at least on receiving a message from the remote server that a connection to the remote server is terminated.

Clause 58. The method of Clause 55, further comprising determining that the first message does not satisfy the condition based at least on the first message being associated with an infusion pump event that is not older than a threshold amount of time.

Clause 59. The method of Clause 55, further comprising determining that the first message does not satisfy the condition based at least on the first message not being a time-sensitive message.

Clause 60. The method of Clause 55, further comprising attempting, prior to determining that the first message does not satisfy the condition, to transmit the first message to the remote server, and determining that the first message was not received by the remote server.

Clause 61. An apparatus configured to provide messaging in a clinical environment, the apparatus comprising: one or more processors; and one or more memories in communication with the one or more processors and storing computer-executable instructions that, when executed by the one or more processors, configure the one or more processors to: cause a plurality of messages to be stored in a message queue, wherein the plurality of messages contain information about one or more infusion pumps residing in the clinical environment, the plurality of messages stored in the message queue including at least a first message; cause at least some of the plurality of messages to be transmitted to a remote server configured to receive messages generated in the clinical environment; subsequent to the transmission, determine that the first message in the message queue does not satisfy a condition for being removed from the message queue; and cause the first message to be transmitted to the remote server such that the first message is received by the remote server.

Clause 62. The apparatus of Clause 61, wherein the computer-executable instructions, when executed by the one or more processors, further configure the one or more processors to detect an interruption in a network connection between the apparatus and the remote server that prevents transmission of messages from the apparatus to the remote server.

Clause 63. The apparatus of Clause 62, wherein the computer-executable instructions, when executed by the one or more processors, further configure the one or more processors to detect the interruption based at least on not having received an acknowledgement from the remote server during a specific time window.

Clause 64. The apparatus of Clause 62, wherein the computer-executable instructions, when executed by the one or more processors, further configure the one or more processors to detect the interruption based at least on receiving a message from the remote server that the network connection between the apparatus and the remote server is terminated.

Clause 65. The apparatus of Clause 61, wherein the computer-executable instructions, when executed by the one or more processors, further configure the one or more processors to determine that the first message does not satisfy the condition based at least on the first message being associated with an infusion pump event that is not older than a threshold amount of time.

Clause 66. The apparatus of Clause 61, wherein the computer-executable instructions, when executed by the one or more processors, further configure the one or more processors to determine that the first message does not satisfy the condition based at least on the first message not being a time-sensitive message.

Clause 67. The apparatus of Clause 61, wherein the computer-executable instructions, when executed by the one or more processors, further configure the one or more processors to attempt, prior to determining that the first message does not satisfy the condition, to transmit the first message to the remote server, and determine that the first message was not received by the remote server.

Clause 68. Non-transitory physical computer storage storing computer-executable instructions that, when executed by one or more computing devices, configure the one or more computing devices to: cause a plurality of messages to be stored in a message queue, wherein the plurality of messages contain information about one or more infusion pumps residing in the clinical environment, the plurality of messages stored in the message queue including at least a first message; cause at least some of the plurality of messages to be transmitted to a remote server configured to receive messages generated in the clinical environment; subsequent to the transmission, determine that the first message in the message queue does not satisfy a condition for being removed from the message queue; and cause the first message to be transmitted to the remote server such that the first message is received by the remote server.

Clause 69. The non-transitory physical computer storage of Clause 68, wherein the computer-executable instructions, when executed by the one or more computing devices, further configure the one or more computing devices to detect an interruption in a network connection to the remote server that prevents transmission of messages to the remote server.

Clause 70. The non-transitory physical computer storage of Clause 69, wherein the computer-executable instructions, when executed by the one or more computing devices, further configure the one or more computing devices to detect the interruption based at least on not having received an acknowledgement from the remote server during a specific time window.

Clause 71. The non-transitory physical computer storage of Clause 69, wherein the computer-executable instructions, when executed by the one or more computing devices, further configure the one or more computing devices to detect the interruption based at least on receiving a message from the remote server that the network connection to the remote server is terminated.

Clause 72. The non-transitory physical computer storage of Clause 68, wherein the computer-executable instructions, when executed by the one or more computing devices, further configure the one or more computing devices to determine that the first message does not satisfy the condition based at least on the first message being associated with an infusion pump event that is not older than a threshold amount of time.

Clause 73. The non-transitory physical computer storage of Clause 68, wherein the computer-executable instructions, when executed by the one or more computing devices, further configure the one or more computing devices to determine that the first message does not satisfy the condition based at least on the first message not being a time-sensitive message.

Clause 74. The non-transitory physical computer storage of Clause 68, wherein the computer-executable instructions, when executed by the one or more computing devices, further configure the one or more computing devices to attempt, prior to determining that the first message does not satisfy the condition, to transmit the first message to the remote server, and determine that the first message was not received by the remote server.

Clause 75. A method for detecting missing messages from a clinical environment, the method comprising: processing a plurality of messages from a network device residing in the clinical environment, wherein the plurality of messages contain information about one or more infusion pumps residing in the clinical environment, wherein the plurality of messages includes a first message having a first message identifier value and a second message having a second message identifier value; determining that one or more messages are missing between the first message and the second message based on (i) receiving the second message after the first message without receiving any other message therebetween and (ii) determining that there is at least one message identifier value between the first message identifier value and the second message identifier value in a predetermined sequence; and transmitting a message request to the network device residing in the clinical environment, wherein the message request identifies the one or more messages that should have been received from the network device but have not been received.

Clause 76. The method of Clause 75, further comprising, in response to the message request, receiving one or more additional messages from the network device, wherein the one or more messages include information that would have been included in the one or more messages.

Clause 77. The method of Clause 76, further comprising updating, based at least on the one or more additional messages received in response to the message request, a cache to include additional information about the one or more infusion pumps residing in the clinical environment.

Clause 78. The method of Clause 75, further comprising causing the network device to request additional information from the one or more infusion pumps that would have been included in the one or more messages.

Clause 79. The method of Clause 75, further comprising, in response to determining that the one or more messages has reached a threshold count, transmitting the message request to the network device residing in the clinical environment.

Clause 80. A system configured to detect missing messages from a clinical environment, the system comprising: one or more processors; and one or more memories in communication with the one or more processors and storing computer-executable instructions that, when executed by the one or more processors, configure the one or more processors to: process a plurality of messages from a network device residing in the clinical environment, wherein the plurality of messages contain information about one or more infusion pumps residing in the clinical environment; detect one or more missing messages that should have been received from the network device but have not been received; and cause a message request to be transmitted to the network device residing in the clinical environment, wherein the message request identifies the one or more missing messages that should have been received from the network device but have not been received.

Clause 81. The system of Clause 80, wherein the computer-executable instructions, when executed by the one or more processors, further configure the one or more processors to receive, in response to the message request, one or more additional messages from the network device, wherein the one or more messages include information that would have been included in the one or more missing messages.

Clause 82. The system of Clause 81, wherein the computer-executable instructions, when executed by the one or more processors, further configure the one or more processors to cause, based at least on the one or more additional messages received in response to the message request, a cache to be updated to include additional information about the one or more infusion pumps residing in the clinical environment.

Clause 83. The system of Clause 80, wherein the computer-executable instructions, when executed by the one or more processors, further configure the one or more processors to detect the one or more missing messages based at least on message identifier information associated with one or more of the plurality of messages.

Clause 84. The system of Clause 80, wherein the computer-executable instructions, when executed by the one or more processors, further configure the one or more processors to detect the one or more missing messages based at least on a first message in the plurality of messages having a message identifier that does not immediately follow another message identifier of a second message of the plurality of messages that immediately follows the first message.

Clause 85. The system of Clause 80, wherein the computer-executable instructions, when executed by the one or more processors, further configure the one or more processors to cause the network device to request additional information from the one or more infusion pumps that would have been included in the one or more missing messages.

Clause 86. The system of Clause 80, wherein the computer-executable instructions, when executed by the one or more processors, further configure the one or more processors to cause, in response to determining that the one or more missing messages has reached a threshold count, the message request to be transmitted to the network device residing in the clinical environment.

Clause 87. The system of Clause 80, wherein the message request includes a flag having a value indicating that the message request is a log retrieval request and not live data.

Clause 88. Non-transitory physical computer storage storing computer-executable instructions that, when executed by one or more computing devices, configure the one or more computing devices to: process a plurality of messages from a network device residing in the clinical environment, wherein the plurality of messages contain information about one or more infusion pumps residing in the clinical environment; detect one or more missing messages that should have been received from the network device but have not been received; and cause a message request to be transmitted to the network device residing in the clinical environment, wherein the message request identifies the one or more missing messages that should have been received from the network device but have not been received.

Clause 89. The non-transitory physical computer storage of Clause 88, wherein the computer-executable instructions, when executed by the one or more computing devices, further configure the one or more computing devices to receive, in response to the message request, one or more additional messages from the network device, wherein the one or more messages include information that would have been included in the one or more missing messages.

Clause 90. The non-transitory physical computer storage of Clause 89, wherein the computer-executable instructions, when executed by the one or more computing devices, further configure the one or more computing devices to cause, based at least on the one or more additional messages received in response to the message request, a cache to be updated to include additional information about the one or more infusion pumps residing in the clinical environment.

Clause 91. The non-transitory physical computer storage of Clause 88, wherein the computer-executable instructions, when executed by the one or more computing devices, further configure the one or more computing devices to detect the one or more missing messages based at least on message identifier information associated with one or more of the plurality of messages.

Clause 92. The non-transitory physical computer storage of Clause 88, wherein the computer-executable instructions, when executed by the one or more computing devices, further configure the one or more computing devices to detect the one or more missing messages based at least on a first message in the plurality of messages having a message identifier that does not immediately follow another message identifier of a second message of the plurality of messages that immediately follows the first message.

Clause 93. The non-transitory physical computer storage of Clause 88, wherein the computer-executable instructions, when executed by the one or more computing devices, further configure the one or more computing devices to cause the network device to request additional information from the one or more infusion pumps that would have been included in the one or more missing messages.

Clause 94. The non-transitory physical computer storage of Clause 88, wherein the computer-executable instructions, when executed by the one or more computing devices, further configure the one or more computing devices to cause, in response to determining that the one or more missing messages has reached a threshold count, the message request to be transmitted to the network device residing in the clinical environment.

Clause 95. A method for generating a user interface based on messages from a clinical environment, the method comprising: processing a message from a network device residing in the clinical environment, wherein the message includes information about one or more infusion pumps in communication with the network device in the clinical environment; determining that the information included in the message satisfies a condition for updating a cache to include at least some of the information included in the message, wherein the cache stores information usable to generate user interfaces in response to a request from a computing device residing in the clinical environment; updating the cache to include at least some of the information included in the message from the network device; receiving a request for a user interface from the computing device residing in the clinical environment; accessing, from the updated cache, user interface information to be used to generate the user interface, wherein the user interface information includes at least some of the information that the cache was updated to include; and outputting instructions for displaying the user interface on the computing device, wherein the instructions are based at least on the user interface information accessed from the updated cache.

Clause 96. The method of Clause 95, wherein the message includes information indicating a current state of the one or more infusion pumps.

Clause 97. The method of Clause 95, wherein the cache stores information associated with two or more infusion pumps residing in different medical facilities.

Clause 98. The method of Clause 95, wherein the user interface information includes user interface data previously generated and stored in the cache.

Clause 99. The method of Clause 95, further comprising updating user interface data stored in the cache, and outputting the instructions based at least on the updated user interface data.

Clause 100. The method of Clause 95, wherein the condition is satisfied based on the information in the message being usable to generate one or more user interfaces in response to a request from the clinical environment.

Clause 101. The method of Clause 95, further comprising causing the user interface to be outputted on a display of the computing device.

Clause 102. A system configured to detect missing messages from a clinical environment, the system comprising: one or more processors; and one or more memories in communication with the one or more processors and storing computer-executable instructions that, when executed by the one or more processors, configure the one or more processors to: process a message from a network device residing in the clinical environment, wherein the message includes information about one or more infusion pumps in communication with the network device in the clinical environment; determine that the information included in the message satisfies a condition for updating a cache to include at least some of the information included in the message, wherein the cache stores information usable to generate user interfaces in response to a request from a computing device residing in the clinical environment; cause the cache to be updated to include at least some of information included in the message from the network device; process a request for a user interface from the computing device residing in the clinical environment; access, from the updated cache, user interface information to be used to generate the user interface, wherein the user interface information includes at least some of the information that the cache was updated to include; and output instructions for displaying the user interface on the computing device, wherein the instructions are based at least on the user interface information accessed from the updated cache.

Clause 103. The system of Clause 102, wherein the message includes information indicating a current state of the one or more infusion pumps.

Clause 104. The system of Clause 102, wherein the cache is configured to store information associated with two or more infusion pumps residing in different medical facilities.

Clause 105. The system of Clause 102, wherein the user interface information includes user interface data previously generated and stored in the cache.

Clause 106. The system of Clause 102, wherein the computer-executable instructions, when executed by the one or more processors, further configure the one or more processors to cause user interface data stored in the cache to be updated, and output the instructions based at least on the updated user interface data.

Clause 107. The system of Clause 102, wherein the condition is satisfied based on the information in the message being usable to generate one or more user interfaces in response to a request from the clinical environment.

Clause 108. The system of Clause 102, wherein the computer-executable instructions, when executed by the one or more processors, further configure the one or more processors to cause the user interface to be outputted on a display of the computing device.

Clause 109. Non-transitory physical computer storage storing computer-executable instructions that, when executed by one or more computing devices, configure the one or more computing devices to: process a message from a network device residing in the clinical environment, wherein the message includes information about one or more infusion pumps in communication with the network device in the clinical environment; determine that the information included in the message satisfies a condition for updating a cache to include at least some of the information included in the message, wherein the cache stores information usable to generate user interfaces in response to a request from a computing device residing in the clinical environment; cause the cache to be updated to include at least some of information included in the message from the network device; process a request for a user interface from the computing device residing in the clinical environment; access, from the updated cache, user interface information to be used to generate the user interface, wherein the user interface information includes at least some of the information that the cache was updated to include; and output instructions for displaying the user interface on the computing device, wherein the instructions are based at least on the user interface information accessed from the updated cache.

Clause 110. The non-transitory physical computer storage of Clause 109, wherein the message includes information indicating a current state of the one or more infusion pumps.

Clause 111. The non-transitory physical computer storage of Clause 109, wherein the cache is configured to store information associated with two or more infusion pumps residing in different medical facilities.

Clause 112. The non-transitory physical computer storage of Clause 109, wherein the user interface information includes user interface data previously generated and stored in the cache.

Clause 113. The non-transitory physical computer storage of Clause 109, wherein the computer-executable instructions, when executed by the one or more computing devices, further configure the one or more computing devices to cause user interface data stored in the cache to be updated, and output the instructions based at least on the updated user interface data.

Clause 114. The non-transitory physical computer storage of Clause 109, wherein the condition is satisfied based on the information in the message being usable to generate one or more user interfaces in response to a request from the clinical environment.

Clause 115. A method for converting messages having one message format from infusion pumps residing in a clinical environment into messages having another message format, the method comprising: detecting a first pump protocol used by one or more infusion pumps in the clinical environment, the first pump protocol defining the first message format; generating a message converter configured to convert a pump message having the first message format into a standardized dataset message having a second message format different from the first message format and including at least some additional data or metadata not included in the pump message; receiving a first pump message from an infusion pump in the clinical environment, wherein the infusion pump is configured to generate pump messages using the first pump protocol; converting the first pump message into a standardized dataset message having the second message format using the message converter, wherein the standardized dataset message includes information associated with the infusion pump and includes at least some additional data or metadata not included in the first pump message; and transmitting the standardized dataset message to a remote server configured to receive standardized dataset messages.

Clause 116. The method of Clause 115, wherein the standardized dataset message includes one or more key-value pairs that are not included in the first pump message.

Clause 117. The method of Clause 116, wherein the one or more key-value pairs are each set to a default value or a null value.

Clause 118. The method of Clause 115, wherein the standardized dataset message includes identification data that identifies one or more portions of the standardized dataset message that include new information.

Clause 119. The method of Clause 115, further comprising detecting the first pump protocol based on a protocol identifier associated with the first pump protocol not being on a predetermined list of protocol identifiers.

Clause 120. The method of Clause 119, further comprising subsequent to detecting the first pump protocol, adding the protocol identifier associated with the first pump protocol to the predetermined list of protocol identifiers.

Clause 121. The method of Clause 115, wherein the message converter comprises a software module that is configured to receive a pump message in the first pump protocol as input and output a standardized dataset message based on the pump message.

Clause 122. The method of Clause 115, wherein the message converter is a configuration file downloaded from the remote server.

Clause 123. An apparatus configured to convert messages having one message format from infusion pumps residing in a clinical environment into messages having another message format, the apparatus comprising: one or more processors; and one or more memories in communication with the one or more processors and storing computer-executable instructions that, when executed by the one or more processors, configure the one or more processors to: detect a first pump protocol used by one or more infusion pumps in the clinical environment, the first pump protocol defining a first message format; generate a message converter configured to convert a pump message having the first message format into another message having a second message format different from the first message format and including at least some additional data or metadata not included in the pump message; receive a first message from an infusion pump in the clinical environment, wherein the infusion pump is configured to generate messages using the first pump protocol; cause the first message to be converted into a second message having the second message format using the message converter, wherein the second message includes information associated with the infusion pump and includes at least some additional data or metadata not included in the first message; and cause the second message to be transmitted to a remote server configured to receive messages having the second message format.

Clause 124. The apparatus of Clause 123, wherein the second message includes one or more key-value pairs that are not included in the first message.

Clause 125. The apparatus of Clause 124, wherein the one or more key-value pairs are each set to a default value or a null value.

Clause 126. The apparatus of Clause 123, wherein the second message includes identification data that identifies one or more portions of the second message that include new information.

Clause 127. The apparatus of Clause 123, wherein the computer-executable instructions, when executed by the one or more processors, further configure the one or more processors to detect the first pump protocol based on a protocol identifier associated with the first pump protocol not being on a predetermined list of protocol identifiers.

Clause 128. The apparatus of Clause 123, wherein the computer-executable instructions, when executed by the one or more processors, further configure the one or more processors to, subsequent to detecting the first pump protocol, cause the protocol identifier associated with the first pump protocol to be added to the predetermined list of protocol identifiers.

Clause 129. The apparatus of Clause 123, wherein the message converter comprises a software module that is configured to receive a pump message having the first message format as input and output another message having the second message format based on the pump message.

Clause 130. The apparatus of Clause 123, wherein the message converter is a configuration file downloaded from the remote server.

Clause 131. Non-transitory physical computer storage storing computer-executable instructions that, when executed by one or more computing devices, configure the one or more computing devices to: detect a first pump protocol used by one or more infusion pumps in the clinical environment, the first pump protocol defining a first message format; generate a message converter configured to convert a pump message having the first message format into another message having a second message format different from the first message format and including at least some additional data or metadata not included in the pump message; receive a first message from an infusion pump in the clinical environment, wherein the infusion pump is configured to generate messages using the first pump protocol; cause the first message to be converted into a second message having the second message format using the message converter, wherein the second message includes information associated with the infusion pump and includes at least some additional data or metadata not included in the first message; and cause the second message to be transmitted to a remote server configured to receive messages having the second message format.

Clause 132. The non-transitory physical computer storage of Clause 131, wherein the second message includes one or more key-value pairs that are not included in the first message, the one or more key-value pairs each having a default value or a null value.

Clause 133. The non-transitory physical computer storage of Clause 131, wherein the computer-executable instructions, when executed by the one or more computing devices, further configure the one or more computing devices to detect the first pump protocol based on a protocol identifier associated with the first pump protocol not being on a predetermined list of protocol identifiers, and subsequent to detecting the first pump protocol, cause the protocol identifier associated with the first pump protocol to be added to the predetermined list of protocol identifiers.

Clause 134. The non-transitory physical computer storage of Clause 131, wherein the message converter comprises a software module that is downloaded from the remote server, the message converter being configured to receive a pump message having the first message format as input and output another message having the second message format based on the pump message.

Clause 135. A method for authenticating a network device residing in a clinical environment using a token, the method comprising: processing an authentication request from the network device residing in the clinical environment via a first network connection, wherein the authentication request includes identifying information associated with the clinical environment, and wherein the clinical environment includes one or more infusion pumps in communication with the network device; identifying login credentials to be used to authenticate the network device residing in the clinical environment; transmitting the login credentials to an authentication system configured to authenticate requests from the network device residing in the clinical environment via a second network connection different from the first network connection; receiving a security token from the authentication system, the security token being usable by the network device to transmit requests to the authentication system via the second network connection; and transmitting the security token to the network device residing in the clinical environment via the first network connection.

Clause 136. The method of Clause 135, wherein the first network connection is a WebSocket connection.

Clause 137. The method of Clause 135, wherein the first network connection is secured and authenticated.

Clause 138. The method of Clause 135, further comprising causing the network device residing in the clinical environment to transmit a signed request to the authentication system.

Clause 139. The method of Clause 135, wherein the first network connection and the second network connection are both established over a wide area network.

Clause 140. The method of Clause 135, further comprising receiving a message from the network device residing in the clinical environment via the first network connection, wherein the messages include information associated with the one or more infusion pumps in communication with the network device.

Clause 141. The method of Clause 140, wherein the network device is configured to communicate with the one or more infusion pumps over a local area network.

Clause 142. A system configured to authenticate a network device residing in a clinical environment using a token, the system comprising: one or more processors; and one or more memories in communication with the one or more processors and storing computer-executable instructions that, when executed by the one or more processors, configure the one or more processors to: process an authentication request from the network device residing in the clinical environment via a first network connection, wherein the authentication request includes identifying information associated with the clinical environment, and wherein the clinical environment includes one or more infusion pumps in communication with the network device; identify login credentials to be used to authenticate the network device residing in the clinical environment; cause the login credentials to be transmitted to an authentication system configured to authenticate requests from the network device residing in the clinical environment via a second network connection different from the first network connection; receive a security token from the authentication system, the security token being usable by the network device to transmit requests to the authentication system via the second network connection; and cause the security token to be transmitted to the network device residing in the clinical environment via the first network connection.

Clause 143. The system of Clause 142, wherein the first network connection is a WebSocket connection.

Clause 144. The system of Clause 142, wherein the first network connection is secured and authenticated.

Clause 145. The system of Clause 142, wherein the computer-executable instructions, when executed by the one or more processors, further configure the one or more processors to cause the network device residing in the clinical environment to transmit a signed request to the authentication system.

Clause 146. The system of Clause 142, wherein the first network connection and the second network connection are both established over a wide area network.

Clause 147. The system of Clause 142, wherein the computer-executable instructions, when executed by the one or more processors, further configure the one or more processors to receive a message from the network device residing in the clinical environment via the first network connection, wherein the messages include information associated with the one or more infusion pumps in communication with the network device.

Clause 148. The system of Clause 147, wherein the network device is configured to communicate with the one or more infusion pumps over a local area network.

Clause 149. Non-transitory physical computer storage storing computer-executable instructions that, when executed by one or more computing devices, configure the one or more computing devices to: process an authentication request from the network device residing in the clinical environment via a first network connection, wherein the authentication request includes identifying information associated with the clinical environment, and wherein the clinical environment includes one or more infusion pumps in communication with the network device; identify login credentials to be used to authenticate the network device residing in the clinical environment; cause the login credentials to be transmitted to an authentication system configured to authenticate requests from the network device residing in the clinical environment via a second network connection different from the first network connection; receive a security token from the authentication system, the security token being usable by the network device to transmit requests to the authentication system via the second network connection; and cause the security token to be transmitted to the network device residing in the clinical environment via the first network connection.

Clause 150. The non-transitory physical computer storage of Clause 149, wherein the first network connection is a secured and authenticated WebSocket connection.

Clause 151. The non-transitory physical computer storage of Clause 149, wherein the computer-executable instructions, when executed by the one or more computing devices, further configure the one or more computing devices to cause the network device residing in the clinical environment to transmit a signed request to the authentication system.

Clause 152. The non-transitory physical computer storage of Clause 149, wherein the first network connection and the second network connection are both established over a wide area network.

Clause 153. The non-transitory physical computer storage of Clause 149, wherein the computer-executable instructions, when executed by the one or more computing devices, further configure the one or more computing devices to receive a message from the network device residing in the clinical environment via the first network connection, wherein the messages include information associated with the one or more infusion pumps in communication with the network device.

Clause 154. The non-transitory physical computer storage of Clause 149, wherein the condition is satisfied based on the information in the message being usable to generate one or more user interfaces in response to a request from the clinical environment.

Clause 155. A method for tagging messages from infusion pumps residing in a clinical environment, the method comprising: processing a pump message including information about an infusion pump residing in the clinical environment; tagging the pump message with a facility identifier indicative of a facility associated with the infusion pump and an account identifier indicative of an account associated with the infusion pump, wherein the facility is below the account in a hierarchical structure, and wherein the hierarchical structure includes one or more intermediate levels that are between the facility and the account in the hierarchical structure; and transmitting the tagged pump message to a remote server such that the facility identifier of the tagged pump message and the account identifier of the tagged message need not be changed by the remote server in response to the facility being moved within the hierarchical structure.

Clause 156. The method of Clause 155, wherein the facility identifier and the account identifier are permanent identifiers that are not changed in response to the facility being moved to another system or region in the hierarchical structure.

Clause 157. The method of Clause 155, wherein the infusion pump is configured to generate pump messages without determining the facility associated with the infusion pump or the account associated with the infusion pump.

Clause 158. The method of Clause 155, further comprising determining, in a priority order, whether one or more facility detection indicators correspond to one of a plurality of facility identifiers stored in a database.

Clause 159. The method of Clause 158, further comprising, in response to determining that none of the one or more facility detection indicators corresponds to any of the plurality of facility identifiers stored in the database, tagging the pump message with a default facility identifier indicating that the pump message originated from an infusion pump that is not associated with a known facility.

Clause 160. The method of Clause 155, further comprising tagging the pump message with a first intermediate identifier indicative of a first intermediate level of the one or more intermediate levels such that the tagged pump message includes the facility identifier, the account identifier, and the first intermediate identifier.

Clause 161. The method of Clause 160, in response to determining that the facility is no longer associated with the first intermediate level in the hierarchical structure, updating the first intermediate identifier, such that the tagged pump message includes the updated first intermediate identifier.

Clause 162. The method of Clause 155, wherein processing the pump message comprises converting a message in a first format received from the infusion pump into the pump message in a second format different from the first format.

Clause 163. An apparatus configured to tag messages from infusion pumps residing in a clinical environment, the apparatus comprising: one or more processors; and one or more memories in communication with the one or more processors and storing computer-executable instructions that, when executed by the one or more processors, configure the one or more processors to: process a pump message including information about an infusion pump residing in the clinical environment; cause the pump message to be tagged with a facility identifier indicative of a facility associated with the infusion pump and an account identifier indicative of an account associated with the infusion pump, wherein the facility is below the account in a hierarchical structure, and wherein the message is not tagged with at least one other identifier indicative of an intermediate level that is between the facility and the account in the hierarchical structure; and cause the tagged pump message to be transmitted to a remote server such that the facility identifier of the tagged pump message and the account identifier of the tagged message need not be changed by the remote server in response to the facility being moved within the hierarchical structure.

Clause 164. The apparatus of Clause 163, wherein the facility identifier and the account identifier are permanent identifiers that are not changed in response to the facility being moved within the hierarchical structure.

Clause 165. The apparatus of Clause 163, wherein the facility identifier and the account identifier are permanent identifiers that are not changed in response to the facility being moved to another system or region in the hierarchical structure.

Clause 166. The apparatus of Clause 163, wherein the infusion pump is configured to generate pump messages without determining the facility associated with the infusion pump or the account associated with the infusion pump.

Clause 167. The apparatus of Clause 163, wherein the computer-executable instructions further configure the one or more processors to cause the pump message to be tagged with a first intermediate identifier indicative of a first intermediate level of the one or more intermediate levels such that the tagged pump message includes the facility identifier, the account identifier, and the first intermediate identifier.

Clause 168. The apparatus of Clause 167, wherein the computer-executable instructions further configure the one or more processors to, in response to determining that the facility is no longer associated with the first intermediate level in the hierarchical structure, cause the first intermediate identifier to be updated, such that the tagged pump message includes the updated first intermediate identifier.

Clause 169. The apparatus of Clause 163, wherein processing the pump message comprises converting a message in a first format received from the infusion pump into the pump message in a second format different from the first format.

Clause 170. Non-transitory physical computer storage storing computer-executable instructions that, when executed by one or more computing devices, configure the one or more computing devices to: process a pump message including information about an infusion pump residing in the clinical environment; cause the pump message to be tagged with a facility identifier indicative of a facility associated with the infusion pump and an account identifier indicative of an account associated with the infusion pump, wherein the facility is below the account in a hierarchical structure, and wherein the message is not tagged with at least one other identifier indicative of an intermediate level that is between the facility and the account in the hierarchical structure; and cause the tagged pump message to be transmitted to a remote server such that the facility identifier of the tagged pump message and the account identifier of the tagged message need not be changed by the remote server in response to the facility being moved within the hierarchical structure.

Clause 171. The non-transitory physical computer storage of Clause 170, wherein the facility identifier and the account identifier are permanent identifiers that are not changed in response to the facility being moved to another system or region in the hierarchical structure.

Clause 172. The non-transitory physical computer storage of Clause 170, wherein the infusion pump is configured to generate pump messages without determining the facility associated with the infusion pump or the account associated with the infusion pump.

Clause 173. The non-transitory physical computer storage of Clause 170, wherein the intermediate level in the hierarchical structure is a system associated with the infusion pump or a region associated with the infusion pump.

Clause 174. The non-transitory physical computer storage of Clause 170, wherein processing the pump message comprises converting a message in a first format received from the infusion pump into the pump message in a second format different from the first format.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores on or other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. A method for tagging messages, the method comprising:
   processing a message including information associated with a first device, wherein the first device is associated with (i) a first group at a first hierarchical level and (ii) a second group at a second hierarchical level that includes at least the first group at the first hierarchical level;
   tagging the message with a first hierarchical identifier associated with the first group; and
   transmitting the tagged message to a remote server such that hierarchical identifiers of the message need not be changed by the remote server in response to the first group no longer being associated with the second group at the second hierarchical level, due to the tagged message not having been tagged with a hierarchical identifier associated with the second group.

2. The method of claim 1, wherein the first hierarchical identifier is a permanent identifier that is not changed in response to the first group being moved to a group other than the second group at the second hierarchical level.

3. The method of claim 1, wherein the first device is configured to generate messages without determining which group at the first hierarchical level is associated with the first device.

4. The method of claim 1, further comprising determining, in a priority order, whether one or more group detection indicators associated with the message or the first device correspond to one of a plurality of hierarchical identifiers stored in a database.

5. The method of claim 4, further comprising, in response to determining that none of the one or more group detection indicators associated with the message or the first device corresponds to any of the plurality of hierarchical identifiers stored in the database, tagging the message with a default hierarchical identifier indicating that the message originated from a device that is not associated with a known group at the first hierarchical level.

6. The method of claim 4, wherein the one or more group detection indicators include one or more of (i) an identifier associated with a network port via which the first device is connected, (ii) location data associated with the first device, (iii) an Internet Protocol (IP) address associated with the first device, (iv) an identifier associated with the first device, (v) a Media Access Control (MAC) address associated with the first device, (vi) a Wi-Fi access point associated with the first device, or (vii) a serial number associated with the first device.

7. The method of claim 1, wherein processing the message comprises converting the message in a first format received from the first device into a converted message in a second format different from the first format.

8. An apparatus configured to tag messages, the apparatus comprising:
   one or more processors; and
   one or more memories in communication with the one or more processors and storing computer-executable instructions that, when executed by the one or more processors, configure the one or more processors to at least:
      process a message including information associated with a first device, wherein the first device is associated with (i) a first group at a first hierarchical level and (ii) a second group at a second hierarchical level that includes at least the first group at the first hierarchical level;
      cause the message to be tagged with a first hierarchical identifier associated with the first group; and
      cause the tagged message to be transmitted to a remote server such that hierarchical identifiers of the message need not be changed by the remote server in response to the first group no longer being associated with the second group at the second hierarchical level, due to the tagged message not having been tagged with a hierarchical identifier associated with the second group.

9. The apparatus of claim 8, wherein the first device is configured to generate messages without determining which group at the first hierarchical level is associated with the first device.

10. The apparatus of claim 8, wherein the computer-executable instructions further configure the one or more processors to determine, in a priority order, whether one or more group detection indicators associated with the message or the first device correspond to one of a plurality of hierarchical identifiers stored in a database.

11. The apparatus of claim 10, wherein the computer-executable instructions further configure the one or more processors to, in response to determining that none of the one or more group detection indicators associated with the message or the first device corresponds to any of the plurality of hierarchical identifiers stored in the database, cause the message to be tagged with a default hierarchical identifier indicating that the message originated from a device that is not associated with a known group at the first hierarchical level.

12. The apparatus of claim 10, wherein the one or more group detection indicators include one or more of (i) an identifier associated with a network port via which the first device is connected, (ii) location data associated with the first device, (iii) an Internet Protocol (IP) address associated with the first device, (iv) an identifier associated with the first device, (v) a Media Access Control (MAC) address associated with the first device, (vi) a Wi-Fi access point associated with the first device, or (vii) a serial number associated with the first device.

13. The apparatus of claim 8, wherein processing the message comprises converting the message in a first format received from the first device into a converted message in a second format different from the first format.

14. Non-transitory physical computer storage storing computer-executable instructions that, when executed by one or more computing devices, configure the one or more computing devices to at least:
   process a message including information associated with a first device, wherein the first device is associated with (i) a first group at a first hierarchical level and (ii) a second group at a second hierarchical level that includes at least the first group at the first hierarchical level;
   cause the message to be tagged with a first hierarchical identifier associated with the first group; and
   cause the tagged message to be transmitted to a remote server.

15. The non-transitory physical computer storage of claim 14, wherein the first device is configured to generate messages without determining which group at the first hierarchical level is associated with the first device.

16. The non-transitory physical computer storage of claim 14, wherein the computer-executable instructions further configure the one or more computing devices to determine, in a priority order, whether one or more group detection indicators associated with the message or the first device correspond to one of a plurality of hierarchical identifiers stored in a database.

17. The non-transitory physical computer storage of claim 16, wherein the computer-executable instructions further configure the one or more computing devices to, in response to determining that none of the one or more group detection indicators associated with the message or the first device corresponds to any of the plurality of hierarchical identifiers stored in the database, cause the message to be tagged with a default hierarchical identifier indicating that the message originated from a device that is not associated with a known group at the first hierarchical level.

18. The non-transitory physical computer storage of claim 16, wherein the one or more group detection indicators include one or more of (i) an identifier associated with a network port via which the first device is connected, (ii) location data associated with the first device, (iii) an Internet Protocol (IP) address associated with the first device, (iv) an identifier associated with the first device, (v) a Media Access Control (MAC) address associated with the first device, (vi) a Wi-Fi access point associated with the first device, or (vii) a serial number associated with the first device.

19. The non-transitory physical computer storage of claim 14, wherein the second group belongs to a third group at a third hierarchical level that includes one or more additional groups at the second hierarchical level that are different from the second group.

20. The non-transitory physical computer storage of claim 14, wherein processing the message comprises converting the message in a first format received from the first device into a converted message in a second format different from the first format.

* * * * *